United States Patent
Bal et al.

(10) Patent No.: US 12,102,466 B2
(45) Date of Patent: Oct. 1, 2024

(54) PET IMAGING USING MULTIPLE ORGAN SPECIFIC SHORT CT SCANS

(71) Applicant: Siemens Medical Solutions USA, Inc., Malvern, PA (US)

(72) Inventors: Girish Bal, Knoxville, TN (US); Frank Kehren, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 376 days.

(21) Appl. No.: 17/753,313

(22) PCT Filed: Jan. 28, 2020

(86) PCT No.: PCT/US2020/015399
§ 371 (c)(1),
(2) Date: Feb. 28, 2022

(87) PCT Pub. No.: WO2021/154213
PCT Pub. Date: Aug. 5, 2021

(65) Prior Publication Data
US 2022/0296194 A1    Sep. 22, 2022

(51) Int. Cl.
*G06K 9/00*    (2022.01)
*A61B 6/00*    (2006.01)
(Continued)

(52) U.S. Cl.
CPC ............ *A61B 6/5235* (2013.01); *A61B 6/032* (2013.01); *A61B 6/037* (2013.01); *A61B 6/5258* (2013.01);
(Continued)

(58) Field of Classification Search
CPC ....... A61B 6/5235; A61B 6/032; A61B 6/037; A61B 6/5258; G06T 11/006; G06T 2211/432
See application file for complete search history.

(56) References Cited

U.S. PATENT DOCUMENTS 6,490,476 B1 *  12/2002  Townsend ............. G01T 1/2985
                                                250/363.04
6,856,666 B2 *  2/2005   Lonn .................... A61B 6/5235
                                                378/19
(Continued)

FOREIGN PATENT DOCUMENTS

WO        2009138898        11/2009

OTHER PUBLICATIONS

International Search Report for Corresponding PCT Application No. PCT/US2020/015399, dated Oct. 19, 2020.

(Continued)

*Primary Examiner* — Shervin K Nakhjavan

(57) ABSTRACT

A method of minimizing a patient's exposure to CT scan radiation during the mu-map generation process in a long axial field of view (FOV) PET scan includes performing a long axial FOV PET scan on a patient; performing one or multiple truncated FOV CT scan of a region in the patient's body in which the organs of interest lies; generating a truncated mu-map covering the truncated CT FOV; and generating a mu-map for the whole long axial FOV of the PET scan by extending the truncated mu-map generated from the truncated FOV CT scan by estimating the missing mu-map data using the PET data.

21 Claims, 16 Drawing Sheets

(51) Int. Cl.
*A61B 6/03* (2006.01)
*G06T 11/00* (2006.01)

(52) U.S. Cl.
CPC ....... *G06T 11/006* (2013.01); *G06T 2211/432* (2013.01)

(56) References Cited

U.S. PATENT DOCUMENTS

| | | | |
|---|---|---|---|
| 7,348,564 B2 | 3/2008 | Wollenweber et al. | |
| 7,507,968 B2 * | 3/2009 | Wollenweber | A61B 6/037 378/19 |
| 7,756,315 B2 * | 7/2010 | Hsieh | A61B 6/4085 378/4 |
| 8,155,415 B2 * | 4/2012 | Faul | A61B 6/037 382/128 |
| 8,478,015 B2 * | 7/2013 | Faul | A61B 6/5235 378/4 |
| 8,577,114 B2 * | 11/2013 | Faul | G06T 11/008 382/131 |
| 8,611,628 B2 * | 12/2013 | Hu | G06T 11/006 382/131 |
| 8,620,053 B2 * | 12/2013 | Michel | G06T 11/005 382/131 |
| 9,453,922 B2 * | 9/2016 | Stodilka | A61B 6/03 |
| 9,600,910 B2 | 3/2017 | Wang et al. | |
| 9,706,972 B1 * | 7/2017 | Ahn | A61B 6/502 |
| 10,078,889 B2 * | 9/2018 | Zhu | G06T 5/50 |
| 10,909,731 B2 | 2/2021 | Gu et al. | |
| 2004/0030246 A1 * | 2/2004 | Townsend | A61B 6/482 600/436 |
| 2008/0073543 A1 | 3/2008 | Vija et al. | |
| 2018/0184992 A1 * | 7/2018 | Li | A61B 6/037 |

OTHER PUBLICATIONS

Johan Nuyts et al: "Completation of a Truncated Attenuation Image From the Attenuated PET Emission Data"; IEEE Transactions On Medical Imaging; IEEE Service Center; Piscataway, NJ, US; vol. 32. No. 2.; Feb. 1, 2013 (Feb. 1, 2013); pp. 237-246.

* cited by examiner

PET IMAGING USING MULTIPLE ORGAN SPECIFIC SHORT CT SCANS

FIELD

The present disclosure relates in general to a method for using one or multiple short CT scans whose FOV could be short than the positron emission tomography (PET) scanned FOV and provides PET reconstructed images with minimal artifacts. Further, the truncated part of the CT that was sampled will help to determine if the scatter obtained using the estimated mu-map and PET is correct and can be used to improve the scatter scaling factors, scatter shape and scatter tail fitting. In addition, the estimated mu-map can be compared with the measured truncated mu-map to correct for any system errors in the measured data such as timing offset.

BACKGROUND

CT scanning and PET scanning are well known methods for diagnostic medical imaging. CT scanning employs multiple X-ray images taken in multiple directions to generate a 3-dimensional image or multiple tomographic image "slices." PET scanning employs a gamma-emitting radiopharmaceutical ingested by a patient or injected into a patient. Multiple gamma ray images are taken in multiple directions to generate a 3-dimensional PET image or multiple slices. CT and PET scanning provide different information. For example, CT scanning generally has higher resolution and is superior for providing structural data such as the structure of bones, organs, etc. PET scanning generally has lower resolution but provides more useful information regarding the functional condition of body tissues and systems such as the cardiovascular system. PET is superior for indicating the presence of soft tissue tumors or decreased blood flow to certain organs or areas of the body, for example. The complementary strengths of CT and PET scanning can be provided simultaneously by performing both methods in a single apparatus and imaging session.

PET scanners with longer axial length are getting increasingly popular for whole body imaging. The longer axial length of a PET scanner reduces the scan time for whole body imaging as well as increase the overall sensitivity of the scanner. A CT scan that covers the same scan range as that of the PET field of view (FOV) is used to generate a robust mu-map for attenuation compensation. In the present disclosure, the term CT and mu-map can be used interchangeably.

On the other hand, for organ specific imaging, e.g. cardiac imaging, the axial length of the long PET scanner or multi-bed PET scans is generally longer than the region of the organ of interest in the patient's body and will cover the organ of interest as well as other regions around it. Currently, when PET scanners with long axial FOV are used, the region corresponding to the entire (e.g. full) axial FOV of the scanner is scanned by CT to generate the mu-maps. For example, in a brain scan using a PET scanner with an axial FOV of 26 cm, because the scanner FOV is longer than the patient's brain the region outside the cranium also gets scanned by CT to generate an accurate mu-map. Hence, for PET scanners with longer axial FOV, the current approach results in having to conduct CT scan regions that are not of clinical interest when the region of interest is smaller than the PET scanner FOV. This means that use of longer FOV PET scanners expose the patients to higher CT radiation dose as well as irradiating organs that are adjacent to the region of interest although those organs are not the subject of the clinical test.

Accordingly, there is a need in the art for improved methods for combined PET and CT scanning. It would be particularly beneficial to provide a method for combined PET and CT scanning that can eliminate the need for CT scanning the regions outside the region of interest.

SUMMARY

According to an aspect of the present disclosure, a method for minimizing a patient's exposure to CT scan radiation during the mu-map generation process in a PET scan is disclosed. The disclosed method is useful in PET scanners whose axial field of view (FOV) is particularly longer compared to the volume of interest (VOI) in the patient. The method comprises performing a full axial FOV PET scan of a patient and generating a PET data; performing a truncated FOV CT scan of a VOI in the patient's body in which an organ of interest lies; generating a truncated mu-map covering the truncated FOV of the CT scan, wherein the truncated FOV of the CT scan is shorter than the full axial FOV of the PET scan; generating a truncated PET data that corresponds to the truncated mu-map and reconstructing a PET image of the VOI using the truncated PET data; and generating a mu-map for the full axial FOV of the PET scan by extending the truncated mu-map generated from the truncated FOV CT scan by estimating the missing mu-map data using the PET data.

BRIEF DESCRIPTION OF THE DRAWINGS

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description.

Disclosed herein is a method that allows generation of a mu-map for the corresponding PET scan using a CT scan whose FOV is truncated to be limited to the organ of interest only and then extending the truncated mu-map by estimating the mu-map for the regions that are outside the truncated CT FOV, but still within the PET scan range, using TOF PET data. In other words, CT scan for generating mu-map is truncated to the region in which the organ of interest resides so that the region of the patient's body exposed to radiation during CT scan is minimized. This, however, results in a truncated mu-map that is missing data for the regions outside the CT FOV but still within the PET scan range. Thus, the method of the present disclosure extends the truncated mu-map by estimating the missing mu-map data using TOF PET data.

Figure 1A:
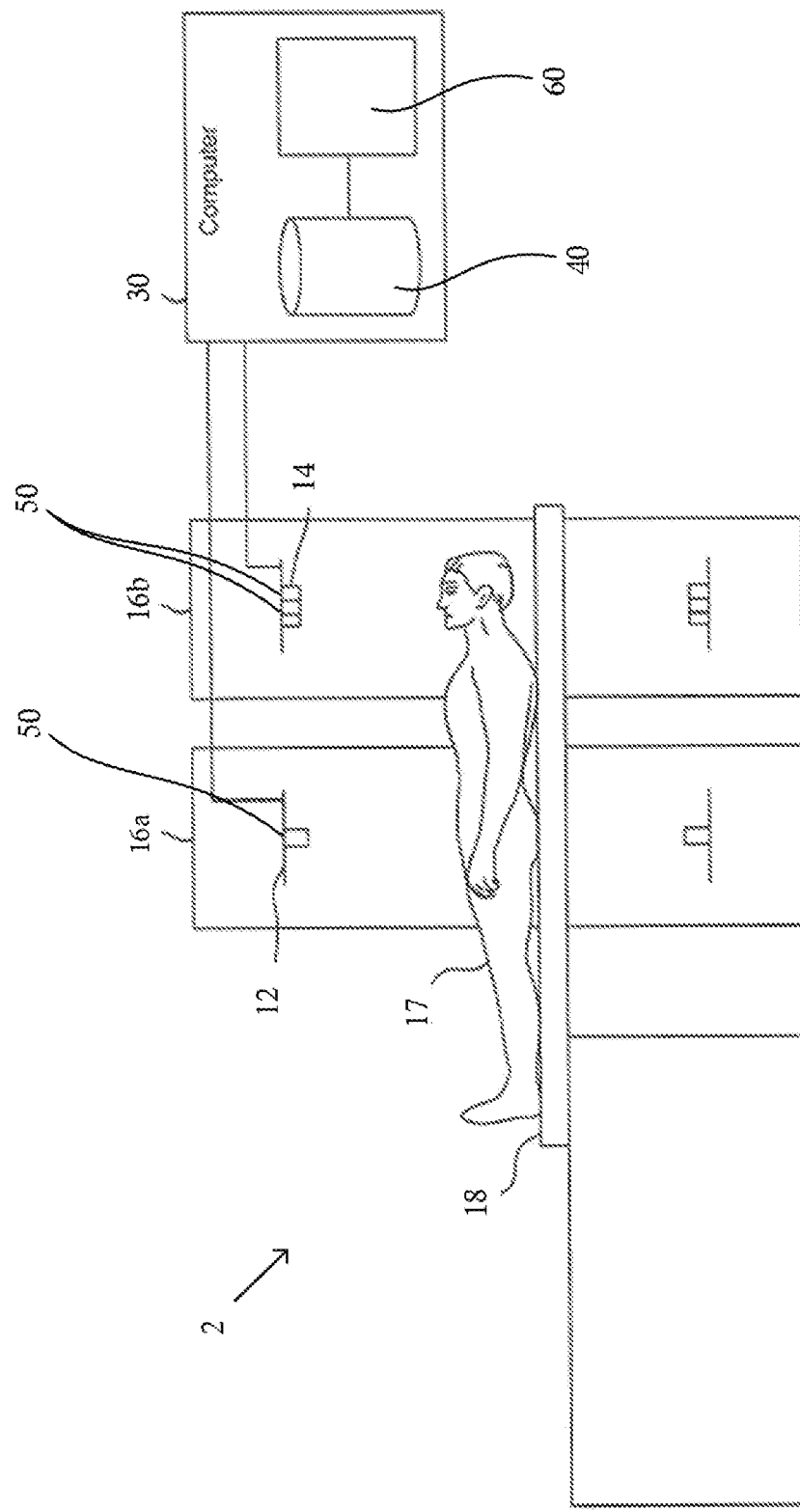
FIG. 1A illustrates a nuclear imaging system for sequentially performing PET and CT scanning, which can be used in accordance with the method of the present disclosure.

FIG. 1A illustrates one embodiment of a nuclear imaging system 2 in which the methods of the present disclosure can be implemented. The nuclear imaging system 2 includes at least a first imaging modality 12 provided in a first gantry 16a. The first imaging modality 12 may include any suitable modality, such as, for example, a computed-tomography (CT) modality, a positron-emission tomography (PET) modality, a single-photon emission computerized tomography (SPECT) modality, etc. The first imaging modality 12 may include a long axial FOV or a short axial FOV. A patient 17 lies on a movable patient bed 18 that may be movable with respect to the first gantry 16a. In some embodiments, the nuclear imaging system 2 includes a second imaging modality 14 provided in a second gantry 16b. The second imaging modality 14 can be any suitable imaging modality, such as, for example, a CT modality, a PET modality, a SPECT modality and/or any other suitable imaging modality. The second modality 14 may include a long axial FOV or a short axial FOV. Each of the first imaging modality 12 and/or the second imaging modality 14 can include one or more detectors 50 arranged, for example, in one or more rings. Each of the detectors 50 is configured to detect an annihilation photon, gamma ray, and/or other nuclear imaging event.

Scan data from the first imaging modality 12 and/or the second imaging modality 14 is stored at one or more computer databases 40 and processed by one or more computer processors 60 of a computer system 30. The graphical depiction of computer system 30 in FIG. 1 is provided by way of illustration only, and computer system 30 may include one or more separate computing devices, for example, as described with respect to FIG. 2. The scan data may be provided by the first imaging modality 12, the second imaging modality 14, and/or may be provided as a separate data set, such as, for example, from a memory coupled to the computer system 30. The computer system 30 can include one or more processing electronics for processing a signal received from one of the plurality of detectors 50.

Figure 1B:
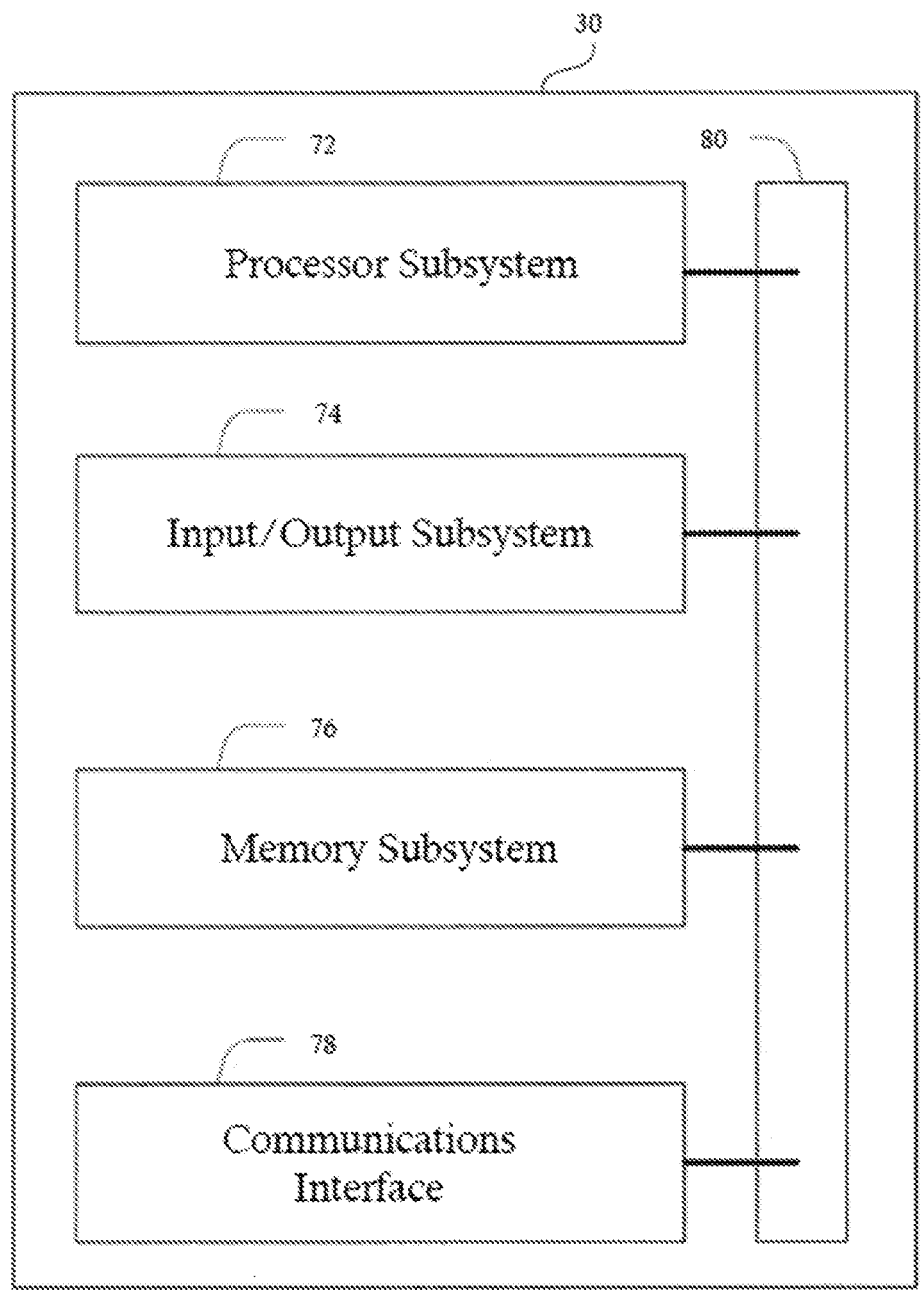
FIG. 1B illustrates a computer system configured to implement one or more embodiments of the method of the present disclosure.

FIG. 1B illustrates a computer system 30 configured to implement one or more processes, in accordance with some embodiments. The system 30 is a representative device and can include a processor subsystem 72, an input/output subsystem 74, a memory subsystem 76, a communications interface 78, and a system bus 80. In some embodiments, one or more than one of the system 30 components can be combined or omitted such as, for example, not including an input/output subsystem 74. In some embodiments, the system 30 can comprise other components not shown in FIG. 1B. For example, the system 30 can also include, for example, a power subsystem. In other embodiments, the system 30 can include several instances of a component shown in FIG. 1B. For example, the system 30 can include multiple memory subsystems 76. For the sake of conciseness and clarity, and not limitation, one of each component is shown in FIG. 1B.

The processor subsystem 72 can include any processing circuitry operative to control the operations and performance of the system 30. In various aspects, the processor subsystem 72 can be implemented as a general purpose processor, a chip multiprocessor (CMP), a dedicated processor, an embedded processor, a digital signal processor (DSP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor subsystem 72 also can be implemented by a controller, a microcontroller, an application specific integrated circuit (ASIC), a field programmable gate array (FPGA), a programmable logic device (PLD), and so forth.

In various aspects, the processor subsystem 72 can be arranged to run an operating system (OS) and various applications. Examples of an OS comprise, for example, operating systems generally known under the trade name of Apple OS, Microsoft Windows OS, Android OS, Linux OS, and any other proprietary or open source OS. Examples of applications comprise, for example, network applications, local applications, data input/output applications, user interaction applications, etc.

In some embodiments, the system 30 can include a system bus 80 that couples various system components including the processing subsystem 72, the input/output subsystem 74, and the memory subsystem 76. The system bus 80 can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCM-CIA), Small Computers Interface (SCSI) or other proprietary bus, or any custom bus suitable for computing device applications.

In some embodiments, the input/output subsystem 74 can include any suitable mechanism or component to enable a user to provide input to system 30 and the system 30 to provide output to the user. For example, the input/output subsystem 74 can include any suitable input mechanism, including but not limited to, a button, keypad, keyboard, click wheel, touch screen, motion sensor, microphone, camera, etc.

In some embodiments, the input/output subsystem 74 can include a visual peripheral output device for providing a display visible to the user. For example, the visual peripheral output device can include a screen such as, for example, a Liquid Crystal Display (LCD) screen. As another example, the visual peripheral output device can include a movable display or projecting system for providing a display of content on a surface remote from the system 30. In some embodiments, the visual peripheral output device can include a coder/decoder, also known as Codecs, to convert digital media data into analog signals. For example, the visual peripheral output device can include video Codecs, audio Codecs, or any other suitable type of Codec.

The visual peripheral output device can include display drivers, circuitry for driving display drivers, or both. The visual peripheral output device can be operative to display content under the direction of the processor subsystem 72. For example, the visual peripheral output device can be able to play media playback information, application screens for application implemented on the system 30, information regarding ongoing communications operations, information regarding incoming communications requests, or device operation screens, to name only a few.

In some embodiments, the communications interface 78 can include any suitable hardware, software, or combination of hardware and software that is capable of coupling the system 30 to one or more networks and/or additional devices. The communications interface 78 can be arranged to operate with any suitable technique for controlling information signals using a desired set of communications protocols, services or operating procedures. The communications interface 78 can include the appropriate physical connectors to connect with a corresponding communications medium, whether wired or wireless.

Vehicles of communication comprise a network. In various aspects, the network can include local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments comprise in-body communications, various devices, and various modes of communications such as wireless communications, wired communications, and combinations of the same.

Wireless communication modes comprise any mode of communication between points (e.g., nodes) that utilize, at least in part, wireless technology including various protocols and combinations of protocols associated with wireless transmission, data, and devices. The points comprise, for example, wireless devices such as wireless headsets, audio and multimedia devices and equipment, such as audio players and multimedia players, telephones, including mobile telephones and cordless telephones, and computers and computer-related devices and components, such as printers, network-connected machinery, and/or any other suitable device or third-party device.

Wired communication modes comprise any mode of communication between points that utilize wired technology including various protocols and combinations of protocols associated with wired transmission, data, and devices. The points comprise, for example, devices such as audio and multimedia devices and equipment, such as audio players and multimedia players, telephones, including mobile telephones and cordless telephones, and computers and computer-related devices and components, such as printers, network-connected machinery, and/or any other suitable device or third-party device. In various implementations, the wired communication modules can communicate in accordance with a number of wired protocols. Examples of wired protocols can include Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, to name only a few examples.

Accordingly, in various aspects, the communications interface 78 can include one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the communications interface 78 can include a wireless interface comprising one or more antennas, transmitters, receivers, transceivers, amplifiers, filters, control logic, and so forth.

In various aspects, the communications interface 78 can provide data communications functionality in accordance with a number of protocols. Examples of protocols can include various wireless local area network (WLAN) protocols, including the Institute of Electrical and Electronics Engineers (IEEE) 802.xx series of protocols, such as IEEE 802.11a/b/g/n/ac, IEEE 802.16, IEEE 802.20, and so forth. Other examples of wireless protocols can include various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols can include wireless personal area network (PAN) protocols, such as an Infrared protocol, a protocol from the Bluetooth Special Interest Group (SIG) series of protocols (e.g., Bluetooth Specification versions 5.0, 6, 7, legacy Bluetooth protocols, etc.) as well as one or more Bluetooth Profiles, and so forth. Yet another example of wireless protocols can include near-field communication techniques and protocols, such as electro-magnetic induction (EMI) techniques. An example of EMI techniques can include passive or active radio-frequency identification (RFID) protocols and devices. Other suitable protocols can include Ultra Wide Band (UWB), Digital Office (DO), Digital Home, Trusted Platform Module (TPM), ZigBee, and so forth.

In some embodiments, at least one non-transitory computer-readable storage medium is provided having computer-executable instructions embodied thereon, wherein, when executed by at least one processor, the computer-executable instructions cause the at least one processor to perform embodiments of the methods described herein. This computer-readable storage medium can be embodied in memory subsystem 76.

In some embodiments, the memory subsystem 76 can include any non-transitory machine-readable or computer-readable media capable of storing data, including both volatile/non-volatile memory and removable/non-removable memory. The memory subsystem 8 can include at least one non-volatile memory unit. The non-volatile memory unit is capable of storing one or more software programs. The software programs can contain, for example, applications, user data, device data, and/or configuration data, or combinations therefore, to name only a few. The software programs can contain instructions executable by the various components of the system 30.

In various aspects, the memory subsystem 76 can include any non-transitory machine-readable or computer-readable media capable of storing data, including both volatile/non-volatile memory and removable/non-removable memory. For example, memory can include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

In one embodiment, the memory subsystem 76 can contain an instruction set, in the form of a file for executing various methods, such as methods including A/B testing and cache optimization, as described herein. The instruction set can be stored in any acceptable form of machine readable instructions, including source code or various appropriate programming languages. Some examples of programming languages that can be used to store the instruction set comprise, but are not limited to: Java, C, C++, C #, Python, Objective-C, Visual Basic, or .NET programming. In some embodiments a compiler or interpreter is comprised to convert the instruction set into machine executable code for execution by the processing subsystem 72.

Figure 2:
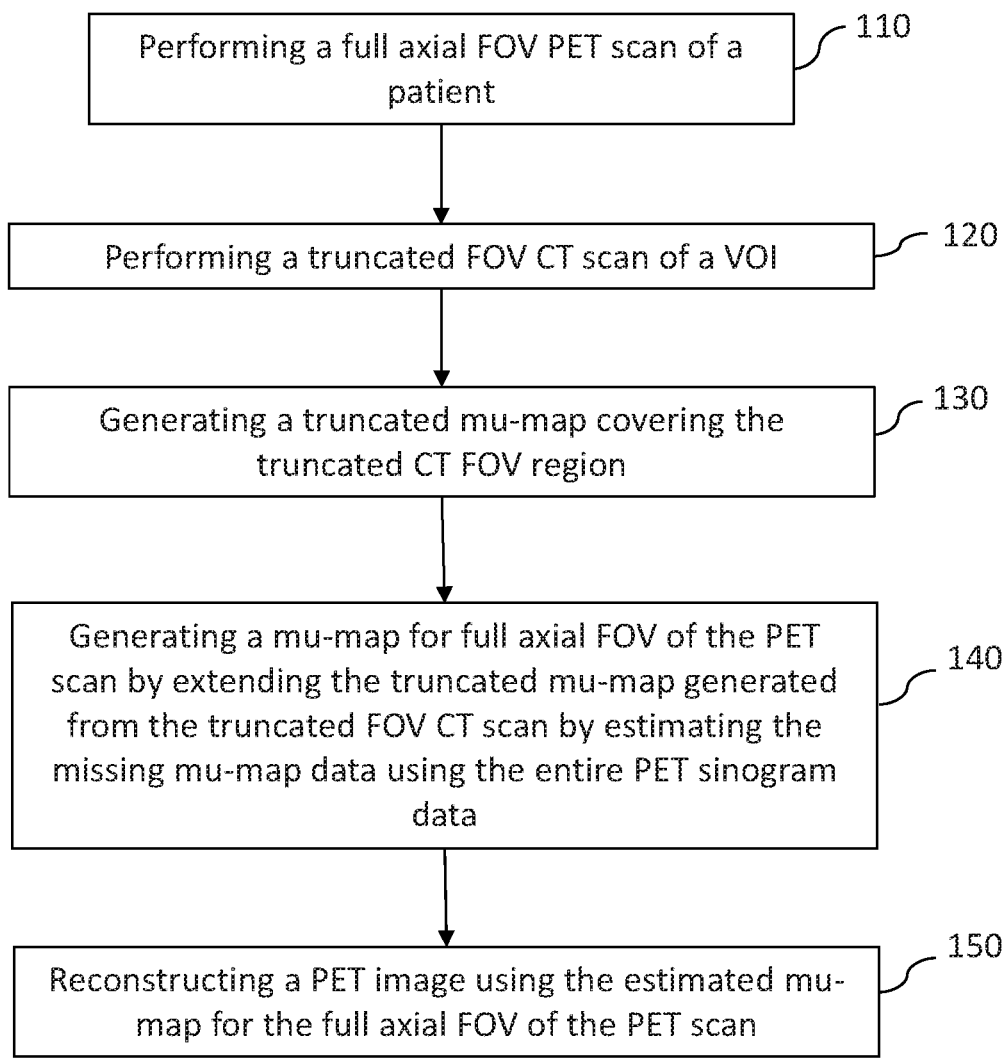
FIG. 2 is a flowchart summarizing the methods according to the present disclosure.

The flowchart 100 of FIG. 2 summarizes an embodiment of the method. First, a full axial FOV PET scan is performed on a patient, thus, generating a PET sinogram data. (See Step 110). The full axial FOV scan can mean one bed position or multiple bed positions. The method then includes performing a truncated FOV CT scan of a region in the patient's body in which the organ of interest lies (also referred to as a volume-of-interest (VOI) in the patient). (See step 120). Next, the method includes generating a truncated mu-map covering the truncated FOV of the CT scan, wherein the truncated FOV of the CT scan is shorter than the full axial FOV of the PET scan. (See Step 130). In this embodiment, the truncated CT FOV is fully within the single FOV of the PET scan. Because the mu-map generated from the truncated FOV CT scan does not match the full FOV of the long axial FOV PET scan TOF data, the mu-map data from the truncated FOV CT scan is missing data before a mu-map for the full PET FOV can be generated. The method of the present disclosure thus includes generating a mu-map for full axial FOV of the PET scan by extending the truncated mu-map generated from the truncated FOV CT scan by estimating the missing mu-map data using the entire measured TOF PET data from step 110. (See Step 140). The method can further include reconstructing a PET image using the estimated mu-map for full axial FOV of the PET scan (i.e., the mu-map generated in step 140), (See Step 150). The reconstruction step 150 comprises allocating different weights to the information content from the different regions in the estimated mu-map during the PET image reconstruction process. Different weight is assigned to the portions of the full axial FOV mu-map that were generated from the measured truncated FOV CT scan vs. the portions of the full axial FOV mu-map that were generated by estimating the missing mu-map data for the regions between the VOIs that were scanned by the truncated FOV CT scans (i.e. the regions that were not CT scanned).

This approach would be ideal for cases such as cardiac imaging where the cardiac region is located at the center of the single bed FOV and the CT is used to scan only the cardiac region while the mu-values of the rest of the body are jointly estimated using PET data. Some examples of other VOI imaging where this concept of organ specific CT scans can be used are breast scans, brain/prostate/pancreas/liver imaging.

Estimating the missing mu-map data in Step 140 can comprise using a combination of, prior predictions, numerical methods, CT scout scans or artificial intelligence type algorithms. In the examples discussed herein, CT is the modality used for obtaining the anatomical information, it is within the scope of the present disclosure to encompass embodiments where the anatomical information is obtained by using MRI, ultrasound or any other imaging modality or any combination of different modalities.

Estimating the missing mu-map data in Step 140 can also comprise calculating the mean TOF PET emission values within the truncated FOV of the CT scan as well as those outside the truncated FOV of the CT scan and using the mean TOF PET emission values to segment norm corrected PET images by identifying voxels that are above uptake threshold for fat, muscle and lungs and generating a mask used to detect the support of the mu-map in the region of the truncated FOV of the CT scan. This is illustrated using some examples below.

Figure 3A:
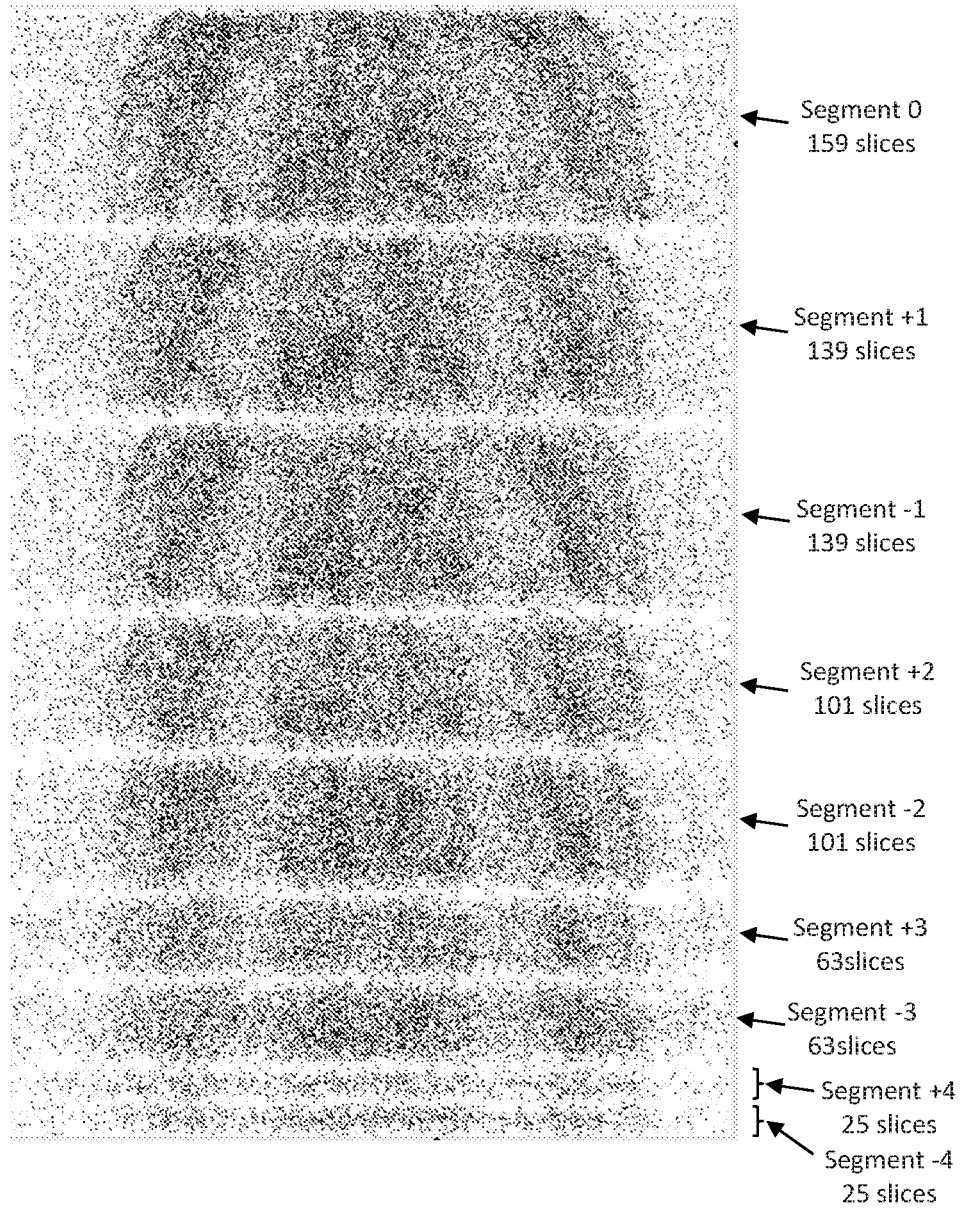
FIG. 3A shows a PET scan projection of a clinical cardiac scan.
Figure 3B:
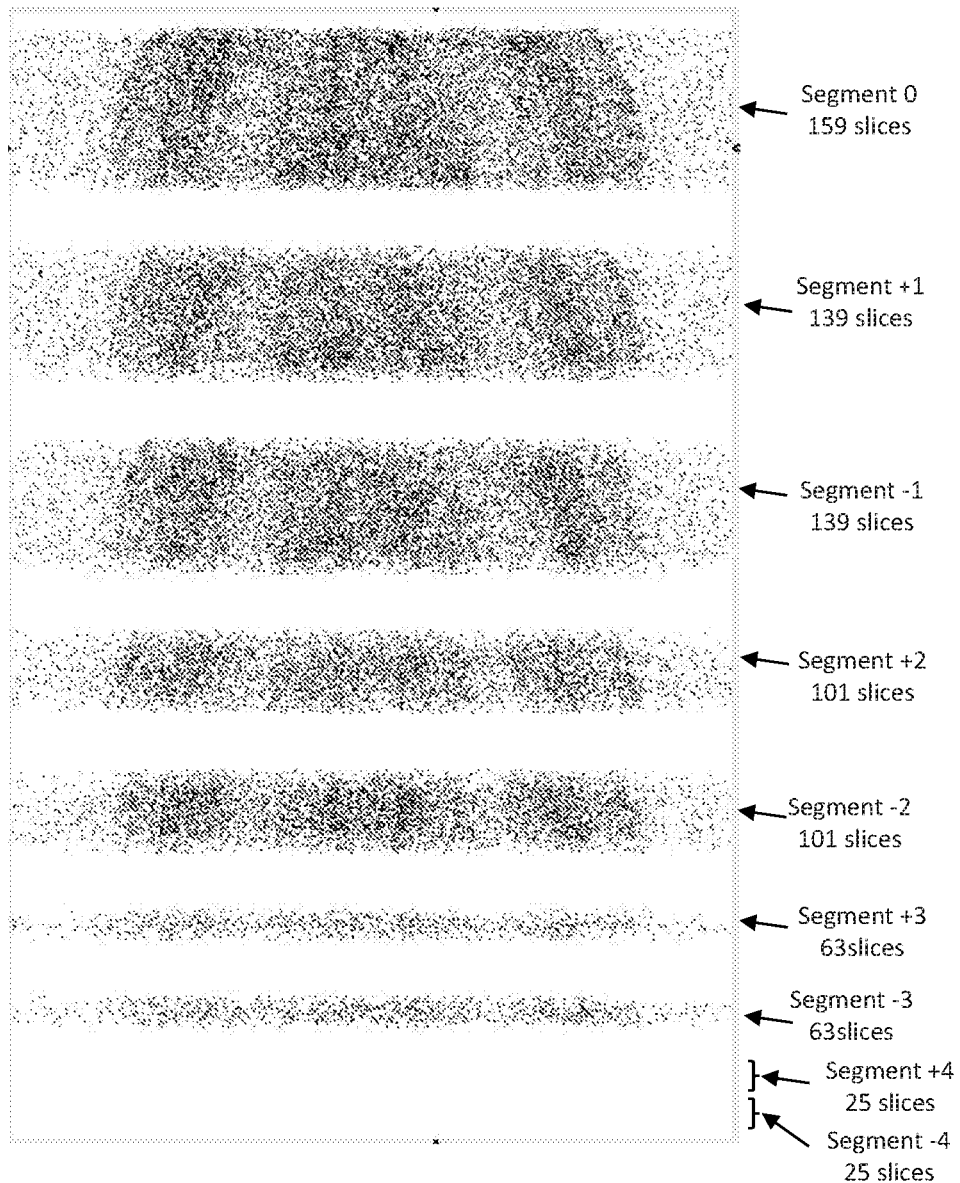
FIG. 3B shows a PET scan projection of the same patient from FIG. 3A after the list-mode data that passes through regions outside the VOI based CT has been turned off.

The process of generating a mu-map for the full axial FOV of the PET scan from the truncated mu-map from the truncated FOV CT scan will now be described in more detail. FIG. 3A shows PET scan projection sinogram of a clinical cardiac scan obtained using Siemens Biograph Vision scanner. The projection data is 520 pixels along the radial direction, 50 angular views, 33 TOF time bins and 815 pixels along the axial direction. FIG. 3B shows a PET scan projection of the same patient from FIG. 3A after the list-mode data that passes through regions outside the CT based VOI has been turned off to simulate a truncated PET scan projections of a VOI corresponding to a truncated FOV CT scan of the VOI The single angular view projection data shown in FIGS. 3A and 3B were obtained by rebinning the list-mode data to 520×815 (159, 139, 139, 101, 101, 63, 63, 25, 25) using span 19. The patient was injected with 373 MBq of FDG and scanned 165 minutes post injection. A two minute Step and Shoot (S&S) scan was performed over the cardiac region to study the uptake in the myocardial region. The list-mode data was rebinned for a maximum ring difference (MRD) of 79, with a TOF mashing factor of 8.

Figure 4A:
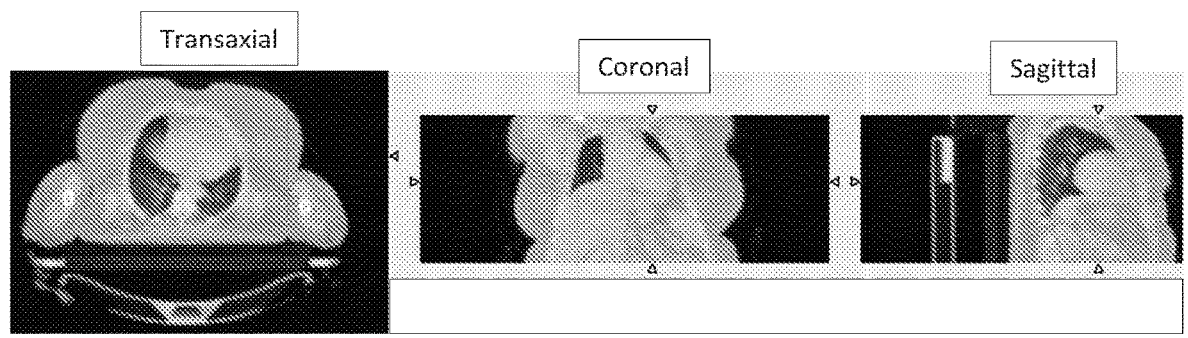
FIG. 4A is a mu-map of a CT scan with the same axial scan length as the PET scan used where the axial length was 159 slices of CT images.

FIG. 4A shows the mu-map of the patient in transaxial, coronal, and sagittal views. The axial length of the mu-map in FIG. 4A is the same as the axial length of the Biograph Vision scanner (26.1 cm) used generate the PET scan projection of FIG. 3A. Then, to study the effects of using a shorter truncated FOV CT scan, 30 slices were removed from the bottom and 10 slices from the top of the CT image. This is done by turning off the list-mode data that passes through regions outside the VOI based CT scan. The resulting PET scan projection sinogram is shown in FIG. 3B. Thus, the sinogram shown in FIG. 3B shows what the PET projection data that matches the truncated FOV CT would look like. This simulates a truncated FOV CT scan with a shorter axial length compared to a single bed PET scan.

Figure 4B:
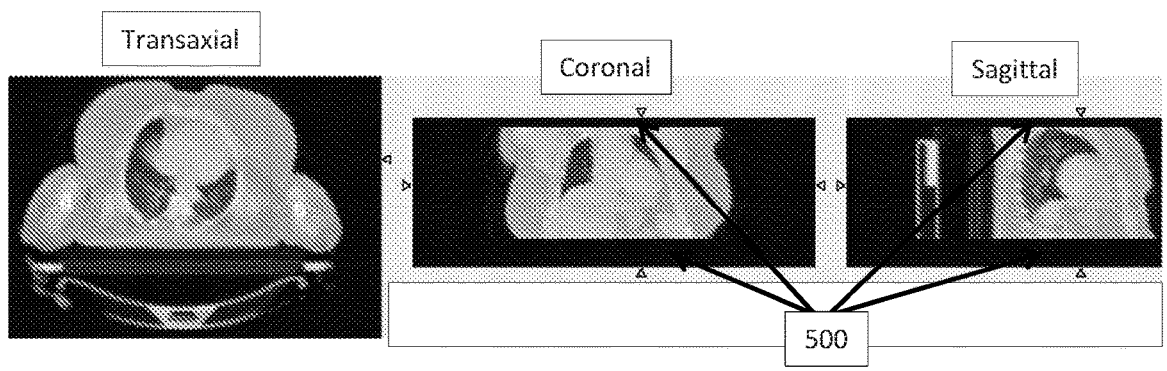
FIG. 4B is a mu-map that represents a mu-map for a truncated CT scan generated by removing 10 slices from the top and 30 slices from the bottom of the CT images to simulate a truncated CT scan with a shorter axial length compared to a single bed PET scan.

FIG. 4A is a mu-map of a CT scan corresponding to the axial scan length of a PET scanner with an axial length of 159 slices. FIG. 4B is a mu-map of a truncated FOV CT scan generated by removing 10 slices of data from the top and 30 slices of data from the bottom of the CT images to simulate a truncated CT scan with a shorter axial length compared to a single bed PET scan. The dark regions 500 in the images are the result of the removed data.

Four approaches were studied for the validation. The PET data were reconstructed using:

(1) the entire mu-map (159 slices) (see FIG. 4A) and the entire PET sinogram to serve as the base reference (see FIG. 3A);

(2) axially truncated mu-map (FIG. 4B) with truncated rebinned PET sinogram that axially matches the CT FOV (FIG. 3B);

(3) axially truncated mu-map (FIG. 4B) and the entire PET sinogram (see FIG. 3A); and (4) axially truncated mu-map combined with estimated mu-map (see FIG. 6C) and the entire sinogram (FIG. 3A).

Figure 5A:
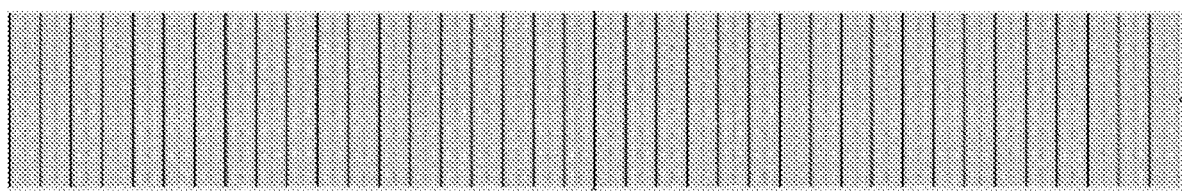
FIG. 5A shows the crystal efficiencies of a PET scanner (in this example 798×80).

FIG. 5A shows the detector crystal efficiencies of a PET scanner. This particular example is from the clinical 8-ring Biograph Vision scanner (798×80). The crystal efficiencies represent the detection efficiencies of each of the crystals in the scanner to the incident photons. For illustration purpose, FIG. 5A illustrates the crystal efficiencies of the PET scanner's detector rings where the group of rings have been unfurled flat. To generate truncated sinograms that matches the truncated FOV CT, the line of response (LOR) outside the CT scan range was removed during the rebinning step by modifying the crystal efficiencies of the scanner. This will be explained below with reference to FIG. 5B. By generating truncated sinograms that exactly match the truncated CT could, in theory, reconstruct converged images without any bias. The effects of the missing data were modeled in the norm during reconstruction.

Figure 5B:
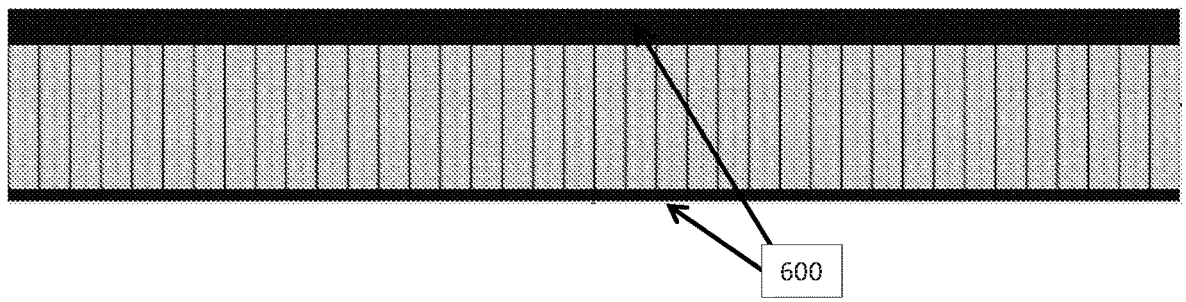
FIG. 5B shows the crystal efficiencies the PET scanner of FIG. 5A when the crystals outside the CT FOV are turned off.

In FIG. 5B, the detector crystal efficiencies of the detector crystals outside the truncated CT axial FOV are turned off. The missing data from the detector crystal rings outside the truncated CT axial FOV are shown as the dark bands 600 along the top and bottom of FIG. 5B. By turning off the crystal efficiencies, the LORs that passes through regions (not measured by the CT) are not considered during reconstruction. In the illustrated example, a band of 15 detector crystal rings at the top and 5 detector crystal rings at the bottom of the scanner were turned off to correspond to the 30 slices and 10 slices of truncated data in the CT image shown in FIG. 4B.

Figure 6A:
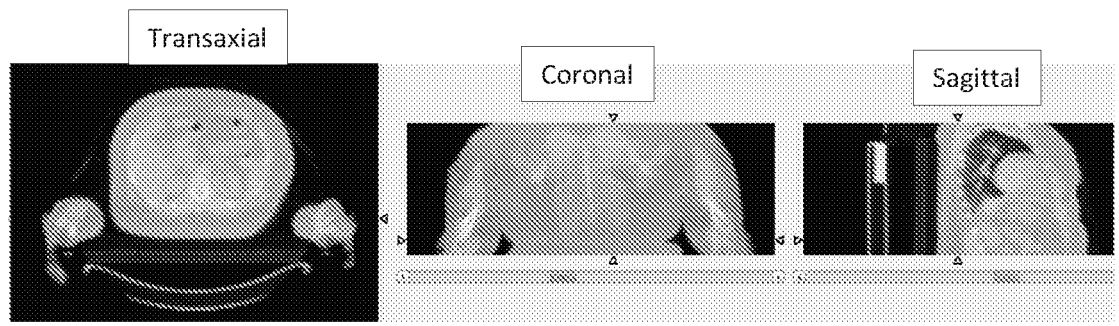
FIG. 6A shows the transaxial, coronal, and sagittal slices through ideal CT scan corresponding to one Vision (Siemens Healthineers) bed with an axial length of 159 slices.
Figure 6B:
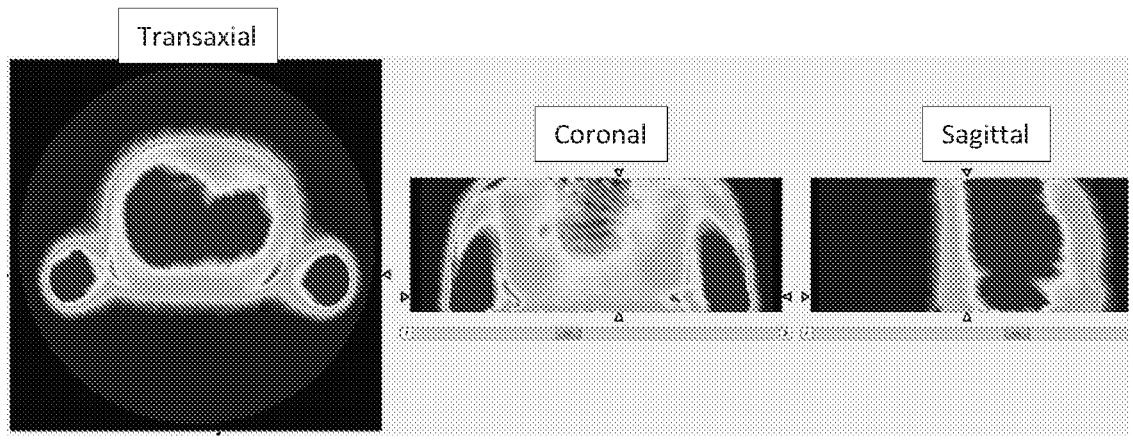
FIG. 6B shows the transaxial, coronal, and sagittal slices through norm corrected TOF back-projected image.

FIG. 6A shows the transaxial, coronal, and sagittal slices through a CT scan corresponding to one Biograph Vision scanner bed with an axial length of 159 slices. To determine the support (e.g. the outline) of the mu-map in the truncated region, the norm corrected PET data is back-projected using non-attenuation correction (NAC) algorithm. The resulting transaxial, coronal, and sagittal slices of the corrected time-of-flight (TOF) back-projected images are shown in FIG. 6B.

Figure 6C:
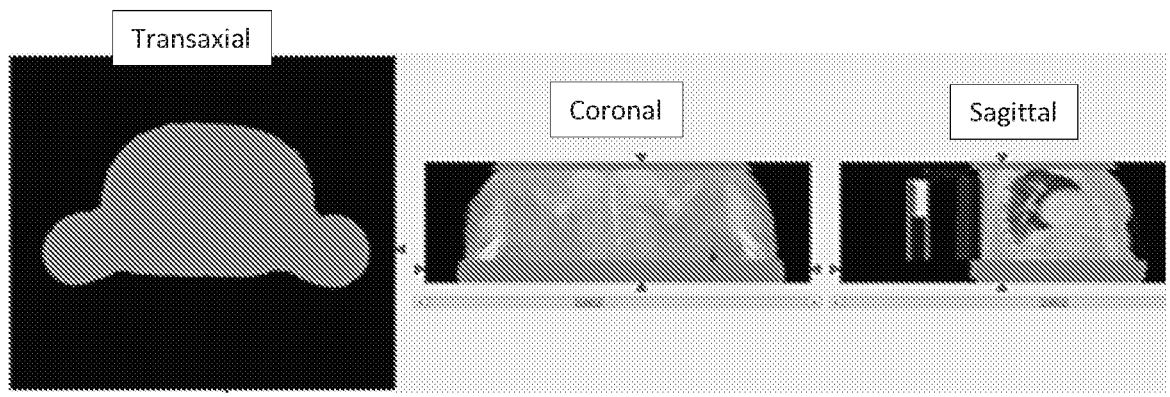
FIG. 6C shows the images in FIG. 5B segmented to generate the mask used to detect the support of the mu-map in the truncated region.

The missing slices of the mu-map are estimated by calculating the mean TOF PET emission values within the truncated FOV of the CT scan as well as those outside the truncated FOV of the CT scan. These mean TOF PET emission values were used to segment the norm corrected PET images from FIG. 6B by identifying the voxels above the uptake threshold for fat, muscle and lungs and generate the mask (e.g. the outline, or a rough approximate region where the attenuating region could be) used to detect the support of the mu-map in the truncated region which is shown in FIG. 6C. Thus, FIG. 6C is the extended mu-map which now includes the attenuation data for the regions that are within the PET scan FOV but outside the truncated FOV of the CT. The missing part of the CT/attenuation map can be estimated using a combination of segmentation, numerical methods, PET data or Artificial Intelligence (AI). Further another approach is to use the scout scan obtained by the CT image to estimate the outline as well as the attenuation along the LOR. The scout scan could be just one view or multiple views. The information from the scout scan can be integrated with the estimation step to generate the estimate mu-map.

The initial support of the mu-map obtained is slightly bigger than the true mu-map measured by CT. This initial support of the mu-map serves as an ideal starting point for advanced joint estimation algorithms such as maximum likelihood reconstruction of attenuation activity (MLAA) and maximum likelihood attenuation correction factor (MLACF) in conjunction with AI based approaches that can be used to determine the extended mu-map.

Modified Ordinary Poisson Maximum Likelihood Expectation Maximization (OP-MLEM) algorithm modeling TOF as well as point-spread-function (PSF) (25 iterations and 1 subset) was used for the PET reconstruction. The modified OP-MLEM update equation is given as the following Equation (1):

$$\lambda^{n+1} = \left[\alpha\lambda^n \frac{1}{BP_{TOF_c}\left(\frac{1}{N_c A_c}\right)} BP_{TOF_c}\left[\frac{Y_c}{FP_{TOF_c}\lambda^n + A_c N_c R_c + A_c S_c}\right]\right] +$$

$$(1-\alpha)\left[\lambda^n \frac{1}{BP_{TOF\_v}(1/N_v A_v)} BP_{TOF\_v}\left[\frac{Y_v}{FP_{TOF\_v}\lambda^n + A_v N_v R_v + A_v S_v}\right]\right]$$

where $\lambda^n$ is the image after n iterations, Y is measured data with the missing data modeled accurately during the TOF mashing step, $BP_{TOF}$ is the TOF back projection and $FP_{TOF}$ is TOF forward projection, R is Randoms, S is scatter, N is norm and A is attenuation, the subscript 'c' stands for complete data and the subscript 'v' stands for virtual gantry generated corresponding to the truncated organ specific CT FOV. This update equation uses multiple sinograms, multiple mu-maps, multiple scatter, and multiple norm for the same image update. Alpha can be multi-dimensional. The above equation is an example to explain the modified OP-MLEM update equation for the reconstruction where the truncated sinogram from the virtual gantry and completely measured data are used along with the truncated mu-map as well as the expanded mu map are used to generate the reconstructed image. Note that the norm, randoms, attenuation and scatter sinograms of the virtual gantry based on the truncated CT data (FIG. 10) and measured sinograms can be different and will be modeled accordingly for the reconstruction. In some embodiments of the present disclosure, the above modified OP-MLEM update equation can also be written as, but not limited to, the following Equation (2):

$$\lambda^{n+1} = \left[\lambda^n \frac{1}{BP_{TOF\_v\_\beta v}(1/N_{av\_\beta c} A_{av\_\beta c})}\right.$$

$$\left. BP_{TOF_{av\_\beta c}}\left[\frac{Y_{av\_\beta c}}{FP_{TOF_{av\_\beta c}}\lambda^n + A_{av\_\beta c} N_{av\_\beta c} R_{av\_\beta c} + A_{av\_\beta c} S_{av\_\beta c}}\right]\right]$$

When the truncated sinogram shown in FIG. 3B was used, the drop in sensitivity due to the missing LORs were modeled during the norm expansion step so as to accurately compensate for the missing data (the missing data represented in FIG. 5B).

Figure 7:
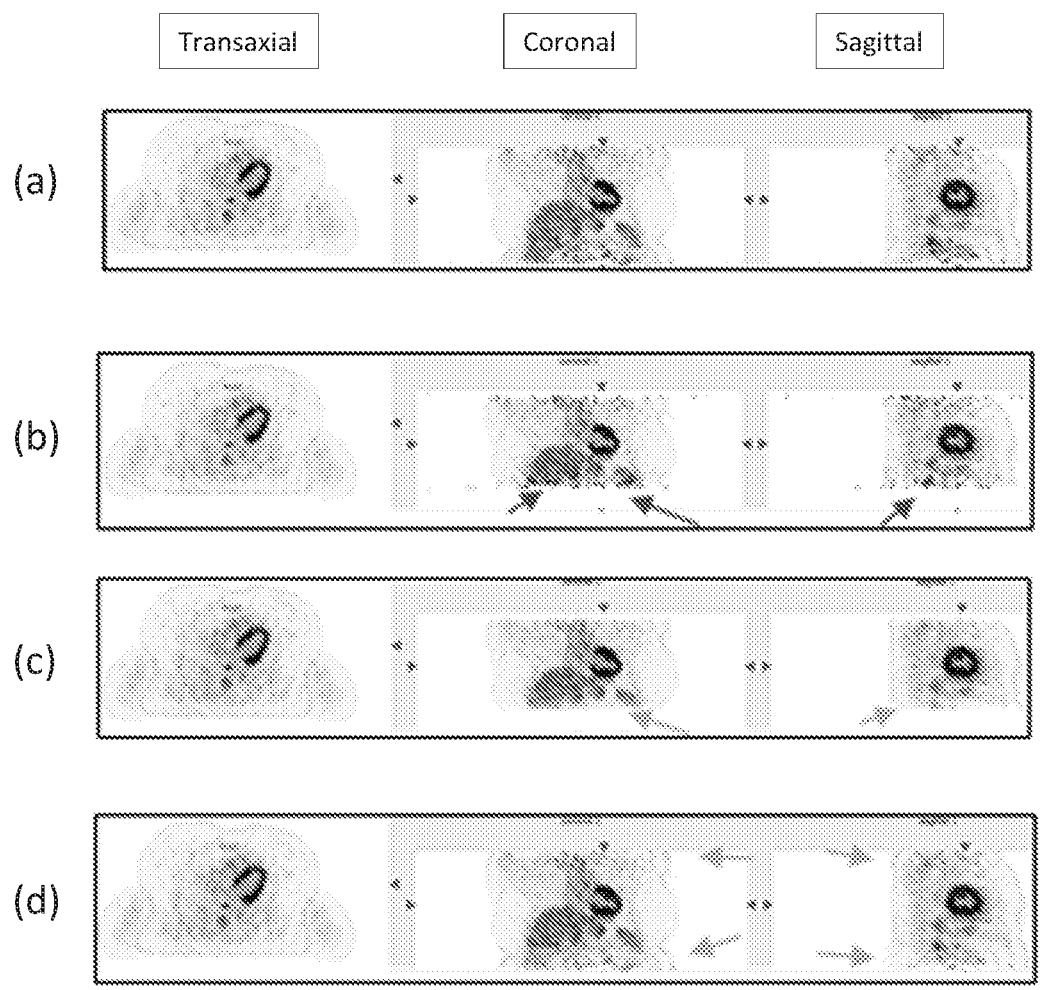
FIG. 7 shows the transaxial, coronal, and sagittal slices through the reconstructed images obtained using (a) Reconstructed image using untruncated sinogram, and untruncated mu-map. (b) Reconstructed image using truncated mu-map and truncated Sinogram that has been rebinned to same axial length as truncated mu-map. (c) Reconstructed image using truncated mu-map and untruncated original Sinogram. (d) Reconstructed image using extended mu-map and untruncated original Sinogram.
Figure 8:
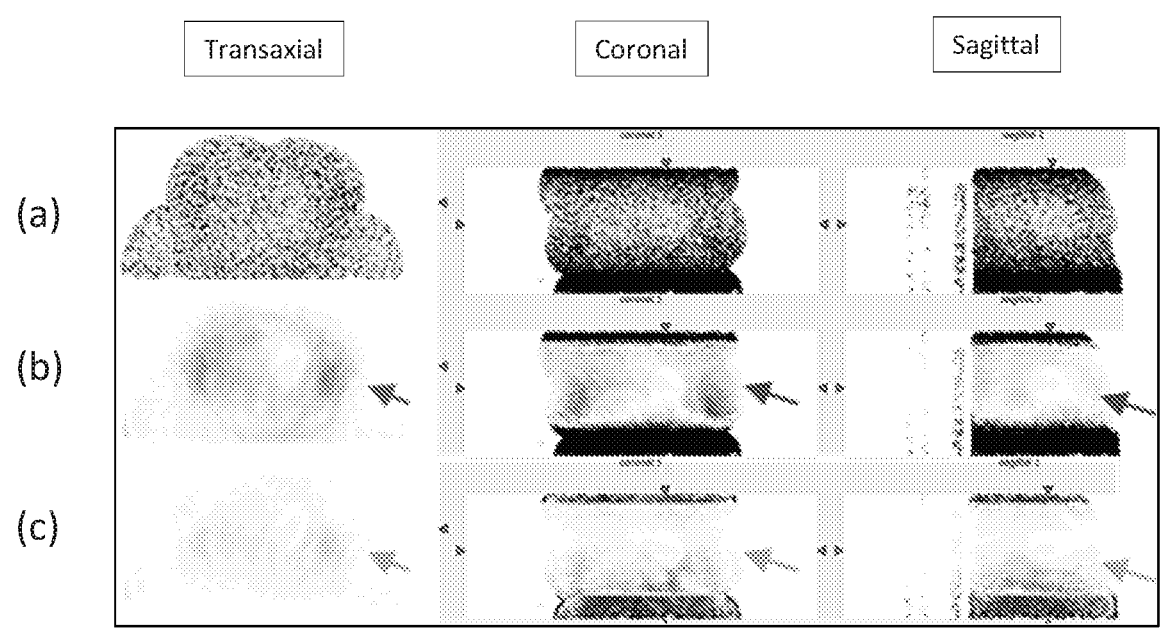
FIG. 8 shows the transaxial, coronal, and sagittal slices through the Absolute Percentage Bias in the reconstructed images. All images were scaled from 0 to 50%. In (a), |bias| % in recon image using truncated sinogram, and truncated mu-map. The voxel by voxel variation is mostly due to the higher statistical variation in the recon image. In (b), lower |bias| % was observed in recon image using truncated mu-map and untruncated original Sinogram (all 80 rings along z-axis). In (c), least |bias| % was present in recon image using calculated extended mu-map and untruncated original Sinogram. Within the myocardial region the |bias| % was less than 2%.

FIG. 7, row (a) shows reconstructed images using complete data (i.e. untruncated sinogram shown in FIG. 3A), and untruncated mu-map (shown in FIG. 4A). This image was used as the baseline to calculate the bias and variance in the reconstructed images obtained using the other approaches. The reconstructed image using truncated mu-map of FIG. 4B and truncated sinogram of FIG. 3B that has been rebinned to same axial length as truncated mu-map is shown in FIG. 7, row (b). This image has higher statistical variation throughout the image and the noisy voxels are more evident at the edge of the organ specific truncated axial CT FOV as noted by the arrows. The increased noise in the reconstructed image is due to the rebinning of the original data such that the LORs that pass outside the truncated short axial CT FOV are removed. This effect can also be seen in the absolute percentage bias image in FIG. 8, row (a). Here, the voxel by voxel absolute percentage bias was calculated between the images shown in FIG. 7, row (b) and FIG. 7, row (a). Further, not modeling the effects of attenuation in the region outside the CT FOV resulted in high bias at the edge slices as shown in the examples in FIG. 8, rows (a) and (b).

Reconstructing the image using truncated mu-map and untruncated original sinogram resulted in less noise as well as bias (compare FIG. 7, row (c) to FIG. 7, row (b)). Note that less noise as well as fewer artifacts are seen at the edge of CT FOV as the entire sinogram was used in the reconstruction. The robustness of the reconstructed image arises from the fact that with the improved TOF timing resolution of 214 picoseconds, the effects of mismatch in the mu-map is very local and hence the error does not propagate much into the PET reconstructed image (within the CT sampled region). Finally, FIG. 7, row (d) shows reconstructed image obtained using the extended mu-map (shown in FIG. 6C) and untruncated original Sinogram (FIG. 3A). The percentage bias as illustrated in FIG. 7, row (c) was found to be least when the extended mu-map was used and the bias in the myocardial region was found to be less than 2%. The arrows in FIG. 7, row (b) shows the high intensity voxels due to truncation of the sinogram and lower counts that are measured from that region while the arrows in FIG. 7, row (c) and row (d) show that the values in those region are more accurate with less noise as the more of the PET data is used during the reconstruction.

By using organ specific truncated FOV CT scan(s) whose axial length is shorter than the full axial FOV PET scan as disclosed, one can reduce the radiation dose to the organs that are outside the VOI during the mu-map generation CT scan. Furthermore, by rebinning the original PET data (full axial FOV data), a virtual gantry can be generated that has the same dimensions as that of the truncated short axis FOV CT (FIG. 3B and FIG. 4B). Reconstructing the corresponding truncated sinogram data provided an unbiased reconstructed image without any systemic artifacts as the short axial CT exactly matched the PET data.

According to some embodiments, the method of flowchart 100 can be implemented in the nuclear imaging system 2 of FIGS. 1A and 1B. Such system can comprise a PET/CT scanner modalities 12, 14, a non-transitory machine-readable storage medium 76, tangibly embodying a program of instructions executable by a processor 60 to cause the processor to perform an operation comprising:

(a) performing a full axial field of view (FOV) PET scan of a patient and generating a PET data;

(b) performing a truncated FOV CT scan of a volume of interest (VOI) in the patient's body;

(c) generating a truncated mu-map covering the truncated FOV of the CT scan, wherein the truncated FOV of the CT scan is shorter than the full axial FOV of the PET scan;

(d) generating a truncated PET data that corresponds to the truncated mu-map and reconstructing a PET image of the VOI using the truncated PET data; and (e) generating a mu-map for full axial FOV of the PET scan by extending the truncated mu-map generated from the truncated FOV CT scan by estimating the missing mu-map data using the PET data.

Figure 9A:
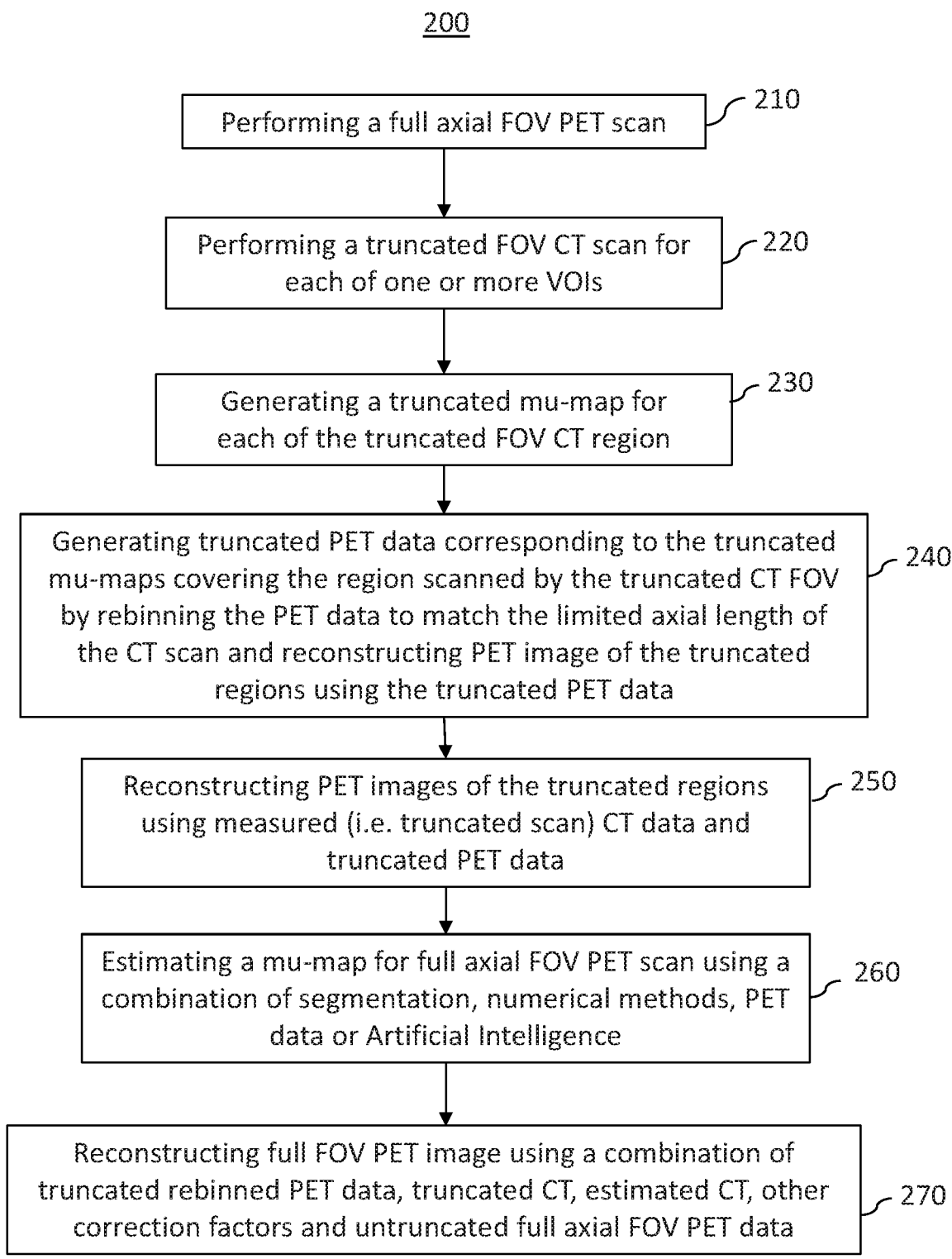
FIG. 9A is a flowchart summarizing a method according to the present disclosure where the proposed approach is used when multiple organs are sampled by the CT independent of each other. The PET scan can be one long axial FOV scan, multiple step-and-shoot scan, or multiple continuous bed motion (CBM) scans.

In some embodiments of the present disclosure, the method of the flowchart 100 can be applied to cases where the full axial FOV PET scan is conducted by a multi-bed scan or a CBM scan. Such method is summarized by the flowchart 200 shown in FIG. 9A. In some embodiments, the method comprises: performing a full axial FOV PET scan of a patient (the full axial FOV PET scan can be, but not limited to, single-bed scan, multi-bed scan, or CBM scans) which generates a full axial FOV PET scan data, (see Step 210); performing multiple truncated FOV CT scan of different regions in the patient's body in which the organ of interest lies, (see Step 220); generating truncated mu-maps covering the regions scanned by the truncated CT FOV (FIG. 10), (see Step 230); generating truncated PET sinogram data corresponding to the truncated mu-maps covering the region scanned by the truncated CT FOV by rebinning the full axial FOV PET scan data to match the limited axial length (i.e. the truncated FOV) of the CT scan and reconstructing PET image of the truncated regions using the truncated PET sinogram data, (see Step 240); reconstructing PET images of the truncated regions using the measured (i.e., truncated scan) CT data and truncated PET sinogram data, (see Step 250); estimating the mu-map using a combination of segmentation, numerical methods, PET data or Artificial Intelligence, (see Step 260); and reconstructing the whole body (i.e., full PET FOV) PET image using a combination of truncated rebinned PET scan data, truncated CT scan data, estimated CT data of the non-scanned region, other correction factors and untruncated measured PET scan data, (see Step 270).

According to some embodiments, the method of flowchart 200 can be implemented in the nuclear imaging system 2 of FIGS. 1A and 1B. Such system can comprise a PET/CT scanner modalities 12, 14, a non-transitory machine-readable storage medium 76, tangibly embodying a program of instructions executable by a processor 60 to cause the processor to perform an operation comprising the steps outlined in flowchart 200 described above.

According to some embodiments, the method of flowchart 200 can further comprise the following steps: reconstructing a full FOV PET image using the full axial FOV PET scan data and the mu-map for full axial FOV of the PET scan while the patient is on the patient bed; and if the full FOV PET image exhibits any abnormal uptake in any region that was not scanned by the truncated FOV CT scan, conducting a truncated FOV CT scan of the region of the abnormal uptake and performing the following to reconstruct a PET image of the region of the abnormal uptake: (i) generating a truncated mu-map from the truncated FOV CT scan of the region of the abnormal uptake; (ii) generating a truncated PET data that corresponds to the truncated mu-map covering the region of the abnormal uptake by rebinning the PET scan data to match the truncated FOV of the truncated FOV CT scan; and (iii) reconstructing PET image of the region of the abnormal uptake using the truncated PET data.

Figure 9B:
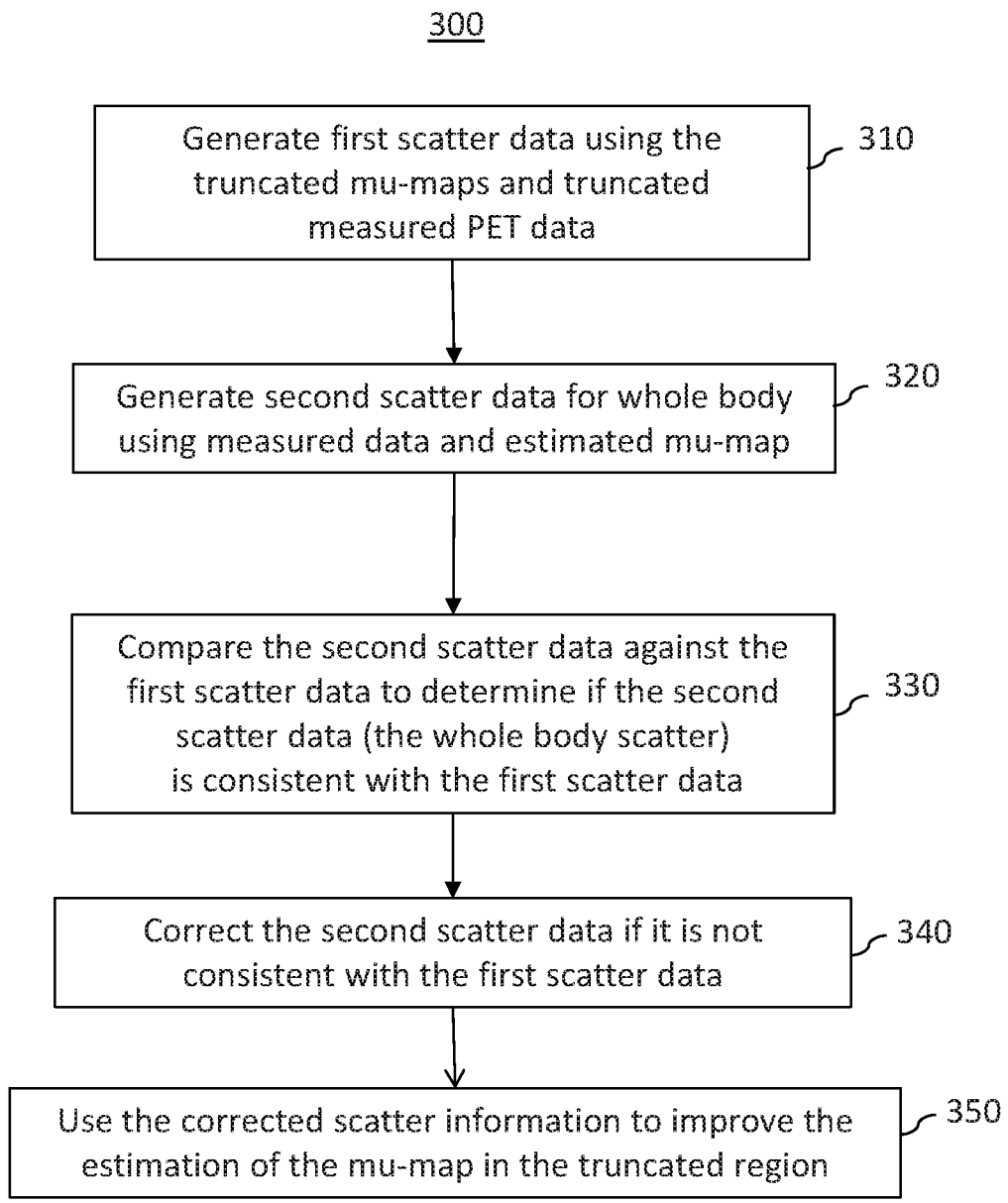
FIG. 9B is a flowchart summarizing a method according to the present disclosure where the proposed approach is used to improve the scatter derived when the estimated extended mu-map is used.

Furthermore, according to another embodiment of the present disclosure, the truncated mu-map generated in the embodiments of the process outlined in flowchart 100 or flowchart 200 can be used to improve the scatter sinogram data obtained using the estimated mu-map. FIG. 9B is a flowchart 300 outlining such method for improving the scatter sinogram data. A first scatter sinogram data is generated using the truncated mu-maps (i.e. the mu-maps generated from the truncated FOV CT scan) (e.g. FIG. 4B) and the truncated rebinned measured PET sinogram data (e.g. FIG. 3B), (See Step 310). Then, a second scatter sinogram data is generated for the whole body using the complete measured full axial FOV PET sinogram data (e.g. FIG. 3A), and the estimated mu-map for the full axial FOV (e.g. FIG. 6C) with or without the truncated mu-map. (See Step 320). Next, the second scatter sinogram data is compared against the first scatter sinogram data to determine if the second scatter sinogram data (the whole body scatter) is consistent with the first scatter sinogram data. (See Step 330). Since the mu-map for the full axial FOV includes portions that are estimated, the scatter sinogram from the estimated portion of the mu-map could be different. If the second scatter sinogram data is not consistent with the first scatter sinogram data, use the first scatter sinogram data (the scatter data from the truncated mu-map (e.g. FIG. 4B)) and truncated rebinned PET sinogram data (e.g. FIG. 3B) to improve or correct the second scatter sinogram data (the whole body scatter data). (See Step 340). The correction could be, but not limited to, improve the scatter scaling, improve the scatter shape, scatter modelling, and improve the overall quantification of the scatter sinogram obtained using the estimated mu-map. The improved/corrected scatter sinogram data can then be used to improve the estimation of (i.e. re-estimate) the mu-map for the truncated FOV CT scanned region of the patient (See Step 350). We can then use the scatter from the re-estimated mu-map to improve the scatter from the truncated mu-map, such as, but not limited to, improving the scatter in the edge slices of the truncated mu-map as well as determining the scatter with less statistical variation.

Figure 9C:
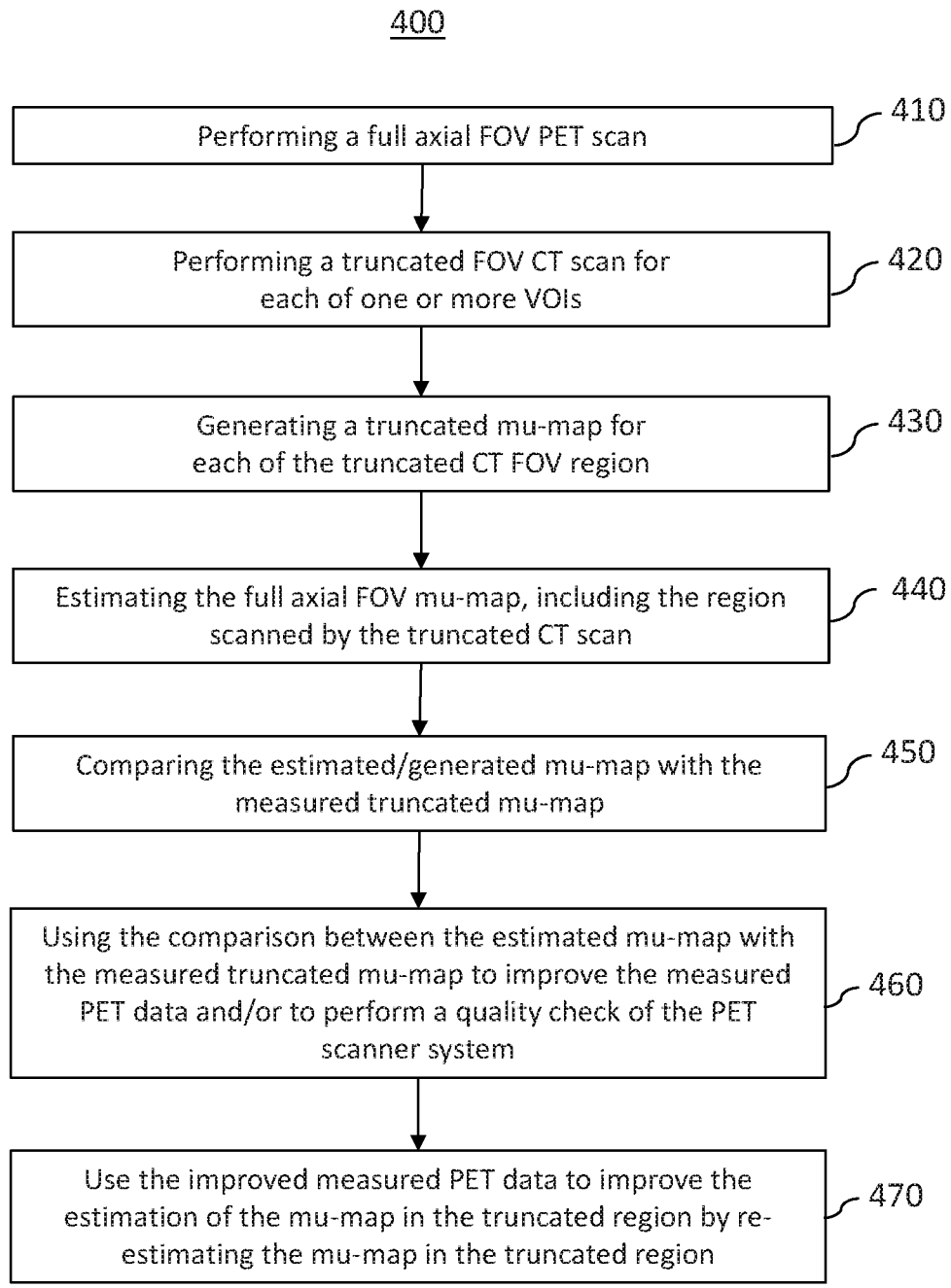
FIG. 9C is a flowchart summarizing a method according to the present disclosure where the proposed approach is used to improve the scanner parameters such as timing resolution, etc.
Figure 10A:
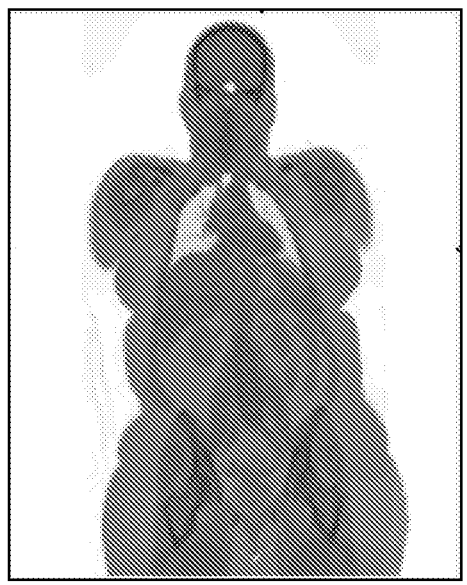
FIG. 10A shows a complete mu-map of a patient that was generated from a CT scan that acquired from head to thigh.
Figure 10B:
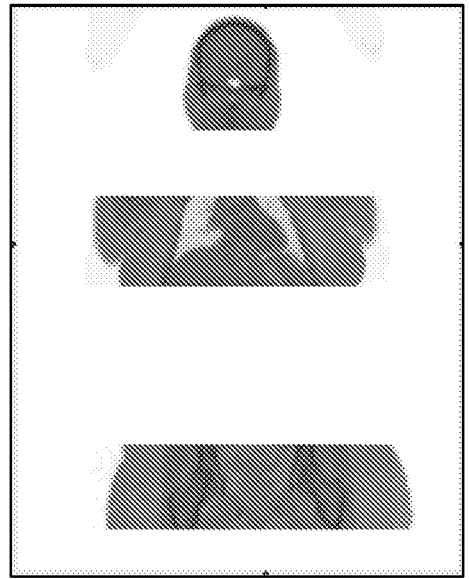
FIG. 10B shows another mu-map of the patient of FIG. 10A that was generated from three separate truncated CT scans, first one of just the brain, second one of just the cardiac region, and third one of just the pelvic region of the patient.

Referring to the flowchart 400 in FIG. 9C, in some embodiments, the concept of using truncated CT scan can be used to detect errors in scanner parameters and fix them. The method outlined in flowchart 400 can be used to check that the PET scanner's imaging parameters are within the tolerance range. The method comprises first performing a full axial FOV PET scan of a patient generating a full axial FOV PET data. (See Step 410). The full axial FOV can be, but not limited to, single bed, multi-bed, or CBM scans. The method then includes performing a truncated FOV CT scan for each of one or more VOIs (each VOI being a region in the patient's body in which an organ of interest lies) (See Step 420). Next, a truncated mu-map is generated for each of the truncated FOV CT scanned region (i.e. the VOI) from the truncated FOV CT scan data. (See Step 430). The measured CT regions (i.e., the truncated FOV CT scanned regions) could be multiple regions in the body apart from each other. e.g. the CT in one scan could be of the brain, heart and pelvis with regions of space not sampled in between. An example of such truncated mu-map is illustrated in FIG. 10B. FIG. 10A shows a complete mu-map of a patient that was acquired from head to thigh. FIG. 10B shows a mu-map from a truncated CT scan that acquired scans of just the brain, the cardiac region, and the pelvic region of the patient. The method outlined in the flowchart 400 also includes using the full axial FOV PET data to estimate the mu-map corresponding to the full axial PET FOV including the region(s) scanned by the truncated FOV CT scan. (See step 440). Next, the method includes comparing the estimated/generated mu-map with the truncated mu-maps (which were generated from the measured truncated FOV CT scan data) to see if the measured full axial FOV PET data is consistent and does not have any artifacts such as time offset error or gantry offset. (See step 450). If any mismatch is observed, one can perform a quality check of the PET scanner system. Further, the data obtained using the measured CT and PET can be used to correct any inconsistencies in the PET scanner system's parameters as well as improve the measured PET scan data. (See step 460). The improved PET scan data can now in turn be used to re-estimate the mu-maps in the truncated FOV CT scanned regions of the patient (i.e. the VOIs). (See step 470).

Another option is to use the truncated mu-map generated from the measured truncated FOV CT scan and compare it against the estimated mu-map to see if the PET scanner imaging parameters (e.g. time offset) are within the desired tolerance range. If the scanner imaging parameters are not within the desired tolerance range, a new calibration should be run for the PET scanner to update the calibration. Thus, an out-of-calibration condition for the PET scanner can be determined without the need to conduct separate QC (quality control) studies.

According to some embodiments, the method of flowchart 400 can be implemented in the nuclear imaging system 2 of FIGS. 1A and 1B. Such system can comprise a PET/CT scanner modalities 12, 14, a non-transitory machine-readable storage medium 76, tangibly embodying a program of instructions executable by a processor 60 to cause the processor to perform an operation comprising the steps outlined in flowchart 400 described above.

Figure 11:
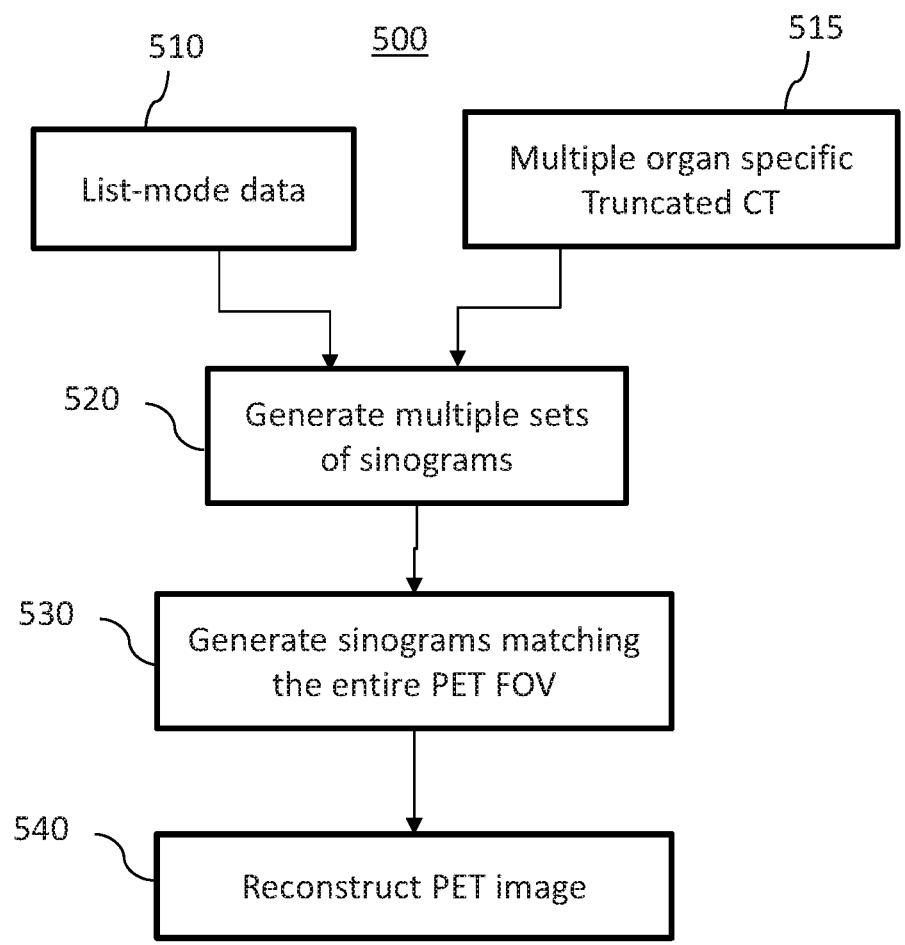
FIG. 11 is a flowchart summarizing an embodiment of the method of the present disclosure where the proposed approach is used to generate multiple sets of list-mode or sinograms that may or may not be limited to the regions covered by CT. The max ring difference (MRD) and span angle used can be different for the different list-mode or sinograms as well as for the entire PET FOV sinogram.

According to some embodiments, the list-mode data from the full axial FOV PET scan can be used directly in the methods of the present disclosure instead of the PET sinogram data. FIG. 11 is a flowchart 500 that outlines the concept. Only the list-mode data 510 that passes through the region measured by the truncated FOV CT scan are identified and used to generate reconstructed PET images corresponding to the region measured by the truncated FOV CT scan. In cases where there are more than one VOI and, thus, a multiple truncated FOV CT scans are performed, one truncated CT scan for each of the VOIs, the same rule is applied for each of the VOI region. In other words, for each of the VOI region, only the list-mode data that passes through that region are identified and used to generate reconstructed PET images corresponding to that VOI region. The remaining list-mode data can be used to estimate the missing mu-map for the regions that the truncated FOV CT scan did not measure. After one or more organ specific truncated FOV CT scans are performed and corresponding truncated mu-maps are generated for each of the truncated FOV CT scanned region (See 515), multiple sets of sinograms are generated. (See 520), one set for each of the CT scanned region, from the list-mode data 510 and the truncated mu-maps. Then, sinograms matching the entire PET FOV (i.e. the full axial FOV PET) are generated. (See 530). From the sinograms matching the entire PET FOV, the full FOV PET image can be reconstructed. (See 540). The multiple list-mode data and sinograms may or may not be limited to the regions measured by the truncated FOV CT. The MRD and span angles used during the reconstruction of the region that is measured by the truncated FOV CT scan as well as the estimated region can be different from each other for the different sinograms as well as the entire PET FOV list-mode data and sinograms.

Figure 12:
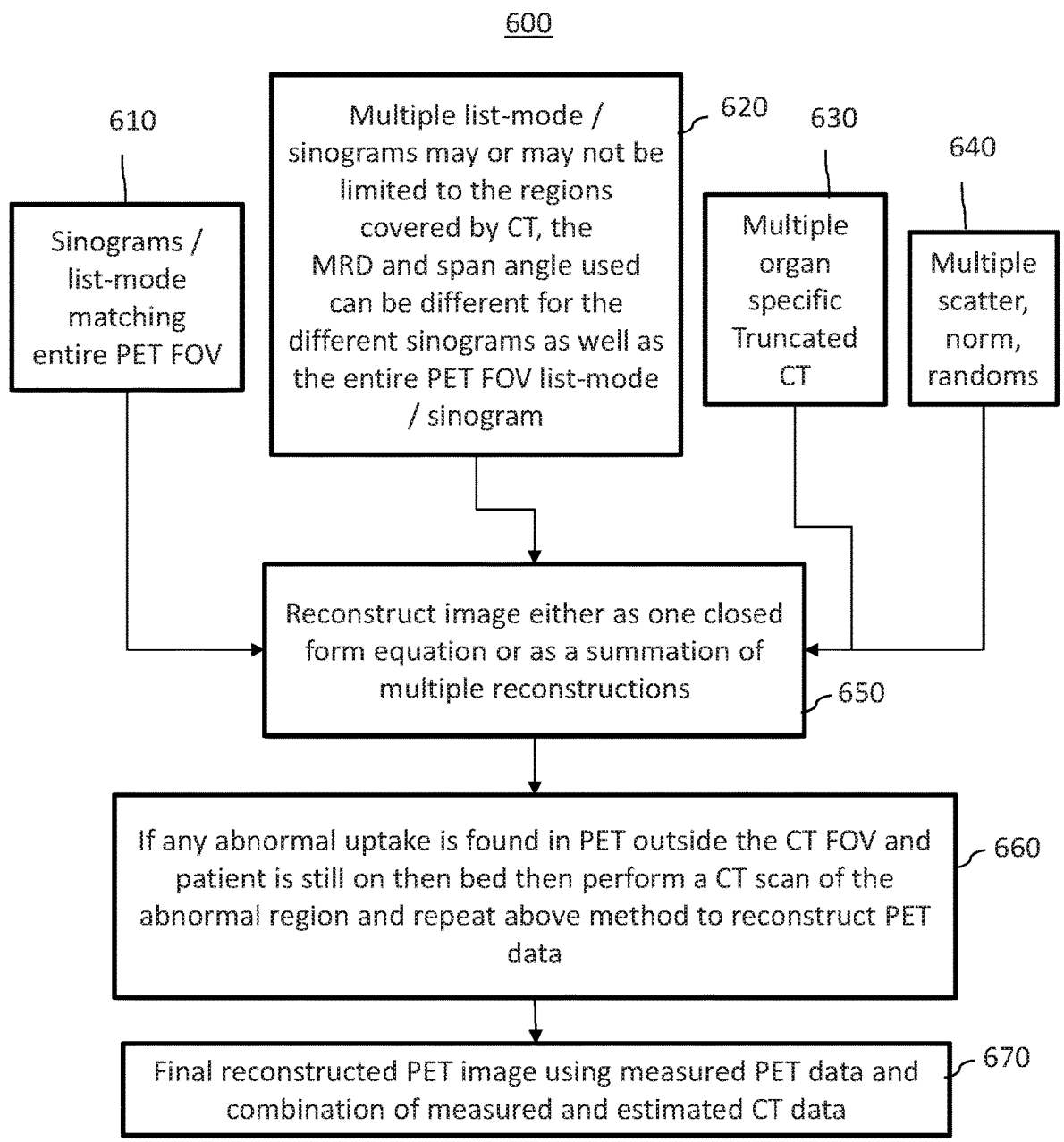
FIG. 12 is a flowchart summarizing an embodiment of the method of the present disclosure where the method of the present disclosure is used to reconstruct a PET image either as one closed form equation or as a summation of multiple reconstructions. It shows if the user desires to CT scan an another region in the patient body while the patient is still on the patient bed, the new information from the CT can be used along with previously acquired data.

As shown in flowchart 600 in FIG. 12, the proposed approach of utilizing the list-mode data and multiple organ specific truncated CT scan data for reconstructing the final PET image is outlined. The reconstruction uses the sinograms/list-mode data that matches the full axial FOV of the PET (See 610), multiple sinograms matching the full axial FOV (See 620), multiple organ specific truncated FOV CT scan of VOIs (See 630), and the correction factors (See 640). The reconstruction of the PET image can be performed either as one closed form equation or as a summation of multiple individual reconstructions. (See 650). Furthermore, if the clinicians observe any abnormalities in the PET image during the scan time, then they can perform an additional CT scan of just the region of the abnormalities (See step 660). For example, if the user desires to CT scan another region in the patient body while the patient is still on the patient bed, the new information from the CT can be used along with previously acquired data and reconstructed. The scanner correction factors 640 such as norm, scatter, randoms can be calculated at the same MRD and span angle as the PET data 610 and they can be different for the various organ specific CT scan region.

According to another embodiment, a method is disclosed that comprises: performing a full axial FOV PET scan of a patient; performing a truncated FOV CT scan of a VOI; generate a mu-map of the CT scanned region; estimate a mu-map for the regions not scanned by the CT; reconstructing a PET image of the full axial FOV, while the patient is still on the patient bed, using a mu-map that is a combination of the mu-map generated from the measured truncated FOV CT scan and the estimated mu-maps while the patient is still on the patient bed; and if the clinician finds any abnormal uptake in any region that was not measured by the CT, then a new truncated FOV CT scan can be performed on just the abnormal region and a mu-map is generated from the new truncated FOV CT scan; then reconstructing a PET image using an updated mu-map for the full axial FOV which now incorporates the mu-map generated from the new truncated FOV CT scan. The updated mu-map for the full axial FOV is a combination of the mu-map generated from the measured new truncated FOV CT scan and estimated mu-maps.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method comprising the steps of:
   (a) performing a full axial field of view (FOV) PET scan of a patient and generating a PET data;
   (b) performing a truncated FOV CT scan of a volume of interest (VOI) in the patient's body;
   (c) generating a truncated mu-map covering the truncated FOV of the CT scan, wherein the truncated FOV of the CT scan is shorter than the full axial FOV of the PET scan;
   (d) generating a truncated PET data that corresponds to the truncated mu-map and reconstructing a PET image of the VOI using the truncated PET data;
   (e) generating a mu-map for full axial FOV of the PET scan by extending the truncated mu-map generated from the truncated FOV CT scan by estimating the missing mu-map data using the PET data; and
   (f) reconstructing a PET image using the mu-map for full axial FOV of the PET scan by allocating different weights to the information content from the different regions in the mu-map.

2. The method of claim 1, wherein the PET scan can be a single bed scan, multiple bed scans, or continuous bed motion scan.

3. The method of claim 1, wherein estimating the missing mu-map data comprises using a combination of, prior predictions, numerical methods, CT scout scans or artificial intelligence type algorithms.

4. The method of claim 3, wherein estimating the missing mu-map data comprises calculating mean TOF PET emission values within the truncated FOV of the CT scan as well as those outside the truncated FOV of the CT scan and using the mean TOF PET emission values to segment norm corrected PET images by identifying voxels that are above uptake threshold for fat, muscle and lungs and generating a mask used to detect the support of the mu-map in the truncated FOV of the CT scan.

5. A system comprising:
a PET/CT scanner;
a non-transitory machine-readable storage medium, tangibly embodying a program of instructions executable by a processor to cause the processor to perform an operation comprising:
  (a) performing a full axial field of view (FOV) PET scan of a patient and generating a PET data;
  (b) performing a truncated FOV CT scan of a volume of interest (VOI) in the patient's body;
  (c) generating a truncated mu-map covering the truncated FOV of the CT scan, wherein the truncated FOV of the CT scan is shorter than the full axial FOV of the PET scan;
  (d) generating a truncated PET data that corresponds to the truncated mu-map and reconstructing a PET image of the VOI using the truncated PET data;
  (e) generating a mu-map for full axial FOV of the PET scan by extending the truncated mu-map generated from the truncated FOV CT scan by estimating the missing mu-map data using the PET data; and
  (f) reconstructing a PET image using the mu-map for full axial FOV of the PET scan by allocating different weights to the information content from the different regions in the mu-map.

6. A non-transitory machine-readable storage medium, tangibly embodying a program of instructions executable by a processor to cause the processor to perform an operation comprising:
  (a) performing a full axial field of view (FOV) PET scan of a patient and generating a PET data;
  (b) performing a truncated FOV CT scan of a volume of interest (VOI) in the patient's body;
  (c) generating a truncated mu-map covering the truncated FOV of the CT scan, wherein the truncated FOV of the CT scan is shorter than the full axial FOV of the PET scan;
  (d) generating a truncated PET data that corresponds to the truncated mu-map and reconstructing a PET image of the VOI using the truncated PET data;
  (e) generating a mu-map for full axial FOV of the PET scan by extending the truncated mu-map generated from the truncated FOV CT scan by estimating the missing mu-map data using the PET data; and
  (f) reconstructing a PET image using the mu-map for full axial FOV of the PET scan by allocating different weights to the information content from the different regions in the mu-map.

7. A method comprising the steps of:
  (a) performing a full axial FOV PET scan of a patient and generating a full axial FOV PET data;
  (b) performing a truncated field of view (FOV) CT scan for each of one or more volumes of interest (VOI) in the patient's body in which the organs of interest lies;
  (c) generating a truncated mu-map from each of the truncated FOV CT scans, wherein the truncated FOV of the CT scans can be shorter than the full axial FOV of the PET scan;
  (d) generating a truncated PET data that corresponds to the truncated mu-maps covering the VOI regions scanned by the truncated FOV CT by rebinning the full axial FOV PET data to match the limited axial length of the CT scan and reconstructing PET image of the VOI regions using the truncated PET data; and
  (e) generating a mu-map for full axial FOV of the PET scan by extending the truncated mu-maps generated from each of the truncated FOV CT scan by estimating the missing mu-map data for the regions not covered by the truncated FOV CT scans using the full axial FOV PET data; and
  (f) reconstructing full FOV PET image by assigning different weights to each of the truncated PET data generated for the truncated mu-maps along with the full axial FOV PET data combined with the mu-map for full axial FOV of the PET scan.

8. The method of claim 7, wherein the PET scan can be a full axial FOV PET single bed scan, multiple bed scans, or continuous bed motion (CBM) scans or a combination of multiple bed scans, and CBM scans.

9. The method of claim 7, wherein estimating the mu-map data comprises using a combination of, prior predictions, numerical methods, CT scout scans or artificial intelligence type algorithms and reconstruct the PET image using a combination of truncated PET data, truncated CT, estimated CT, other correction factors and measured PET data.

10. The method of claim 7, further comprising:
  (g) generating a first scatter sinogram data using the truncated mu-maps and the corresponding truncated PET data;
  (b) generating a second scatter sinogram data using the full axial FOV PET data and the mu-map for full axial FOV of the PET scan;
  (c) comparing the second scatter sinogram data against the first scatter sinogram data to determine if the second scatter sinogram data is consistent with the first scatter sinogram data;
  (d) where the second scatter sinogram data is not consistent with the first scatter sinogram data, the first scatter sinogram data and the truncated rebinned PET sinogram data is used to correct the second scatter sinogram data; and
  (e) re-estimate the mu-map for the truncated FOV CT scanned region of the patient using the corrected second scatter sinogram data.

11. The method of claim 10, further comprising using the re-estimated mu-map for the truncated FOV CT scanned region of the patient to improve scatter correction for the truncated mu-map.

12. The method of claim 7, further comprising:
  (f) reconstructing a full FOV PET image using the full axial FOV PET scan data and the mu-map for full axial FOV of the PET scan while the patient is on the patient bed; and
  (g) if the full FOV PET image exhibits any abnormal uptake in any region that was not scanned by the truncated FOV CT scan, conducting a truncated FOV CT scan of the region of the abnormal uptake and performing the following:

(h) generating a truncated mu-map from the truncated FOV CT scan of the region of the abnormal uptake;

(i) generating a truncated PET data that corresponds to the truncated mu-map covering the region of the abnormal uptake by rebinning the PET scan data to match the truncated FOV of the truncated FOV CT scan; and (j) reconstructing PET image of the region of the abnormal uptake using the truncated PET data.

13. A system comprising:
a PET/CT scanner;
a non-transitory machine-readable storage medium, tangibly embodying a program of instructions executable by a processor to cause the processor to perform an operation comprising:

(a) performing a full axial FOV PET scan of a patient and generating a full axial FOV PET data;

(b) performing a truncated field of view (FOV) CT scan for each of one or more volumes of interest (VOI) in the patient's body in which the organs of interest lies;

(c) generating a truncated mu-map from each of the truncated FOV CT scan, wherein the truncated FOV of the CT scans can be shorter than the full axial FOV of the PET scan;

(d) generating truncated PET data that corresponds to the truncated mu-maps covering the VOI regions scanned by the truncated FOV CT by rebinning the PET data to match the limited axial length of the CT scan and reconstructing PET image of the VOI regions using the truncated PET data;

(e) generating a mu-map for full axial FOV of the PET scan by extending the truncated mu-maps generated from each of the truncated FOV CT scan by estimating the missing mu-map data for the regions not covered by the truncated FOV CT scans using the full axial FOV PET data; and (f) reconstructing full FOV PET image by assigning different weights to each of the truncated PET data generated for the truncated mu-maps along with the full axial FOV PET data combined with the mu-map for full axial FOV of the PET scan.

14. A non-transitory machine-readable storage medium, tangibly embodying a program of instructions executable by a processor to cause the processor to perform an operation comprising:

(a) performing a full axial FOV PET scan of a patient and generating a full axial FOV PET data;

(b) performing a truncated field of view (FOV) CT scan for each of one or more volumes of interest (VOI) in the patient's body in which the organs of interest lies;

(c) generating a truncated mu-map from each of the truncated FOV CT scan, wherein the truncated FOV of the CT scans can be shorter than the full axial FOV of the PET scan;

(d) generating a truncated PET data that corresponds to the truncated mu-maps covering the VOI regions scanned by the truncated FOV CT by rebinning the PET data to match the limited axial length of the CT scan and reconstructing PET image of the VOI regions using the truncated PET data;

(e) generating a mu-map for full axial FOV of the PET scan by extending the truncated mu-maps generated from each of the truncated FOV CT scan by estimating the missing mu-map data for the regions not covered by the truncated FOV CT scans using the full axial FOV PET data; and (f) reconstructing full FOV PET image by assigning different weights to each of the truncated PET data generated for the truncated mu-maps along with the full axial FOV PET data combined with the mu-map for full axial FOV of the PET scan.

15. A method comprising the steps of:

(a) performing a full axial field of view (FOV) PET scan of a patient using a PET scanner system and generating measured full axial FOV PET scan data;

(b) performing a truncated FOV CT scan for each of one or more volumes of interest (VOI);

(c) generating a truncated mu-map from the truncated FOV CT scan data for each of the VOI region;

(d) using the measured full axial FOV PET scan data to estimate a mu-map corresponding to the full axial PET FOV including the regions scanned by the truncated FOV CT scan;

(e) comparing the estimated mu-map with the truncated mu-maps to detect any inconsistencies in the measured full axial FOV PET scan data that are caused by artifacts such as time offset error or gantry offset; and (f) performing a quality check of the PET scanner system if any inconsistencies between the estimated mu-map and the truncated mu-maps are detected.

16. The method of claim 15, wherein the full axial FOV PET scan can be a single bed scan, multiple bed scan, or continuous bed motion scan.

17. The method of claim 15, further comprising using the detected inconsistencies between the estimated mu-map and the truncated mu-maps to correct any inconsistencies in the PET scanner system's parameters and improve the measured full axial FOV PET scan data.

18. The method of claim 17, further comprising using the improved measured full axial FOV PET scan data to re-estimate the mu-maps for VOIs.

19. The method of claim 15, further comprising using the detected inconsistencies between the estimated mu-map and the truncated mu-maps to determine whether the PET scanner requires calibration.

20. A system comprising:
a PET/CT scanner;
a non-transitory machine-readable storage medium, tangibly embodying a program of instructions executable by a processor to cause the processor to perform an operation comprising:

(a) performing a full axial field of view (FOV) PET scan of a patient using a PET scanner system and generating measured full axial FOV PET scan data;

(b) performing a truncated FOV CT scan for each of one or more volumes of interest (VOI);

(c) generating a truncated mu-map from the truncated FOV CT scan data for each of the VOI region;

(d) using the measured full axial FOV PET scan data to estimate a mu-map corresponding to the full axial PET FOV including the regions scanned by the truncated FOV CT scan;

(e) comparing the estimated mu-map with the truncated mu-maps to detect any inconsistencies in the measured full axial FOV PET scan data that are caused by artifacts such as time offset error or gantry offset; and (f) performing a quality check of the PET scanner system if any inconsistencies between the estimated mu-map and the truncated mu-maps are detected.

21. A non-transitory machine-readable storage medium, tangibly embodying a program of instructions executable by a processor to cause the processor to perform an operation comprising:

(a) performing a full axial field of view (FOV) PET scan of a patient using a PET scanner system and generating measured full axial FOV PET scan data;
(b) performing a truncated FOV CT scan for each of one or more volumes of interest (VOI);
(c) generating a truncated mu-map from the truncated FOV CT scan data for each of the VOI region;
(d) using the measured full axial FOV PET scan data to estimate a mu-map corresponding to the full axial PET FOV including the regions scanned by the truncated FOV CT scan;
(e) comparing the estimated mu-map with the truncated mu-maps to detect any inconsistencies in the measured full axial FOV PET scan data that are caused by artifacts such as time offset error or gantry offset; and
(f) performing a quality check of the PET scanner system if any inconsistencies between the estimated mu-map and the truncated mu-maps are detected.

\* \* \* \* \*